(12) United States Patent
Aubert

(10) Patent No.: US 12,409,245 B2
(45) Date of Patent: Sep. 9, 2025

(54) COMBINATION ULTRA-VIOLET A (UVA) AND ULTRA-VIOLET C (UVC) SYSTEM FOR REDUCTION AND INHIBITION OF GROWTH OF PATHOGENS

(71) Applicant: Helios Shield Ltd, London (GB)

(72) Inventor: Andrew Clark Baird Aubert, Waterdown (CA)

(73) Assignee: Helios Shield Ltd., London (GB)

( * ) Notice: Subject to any disclaimer, the term of this patent is extended or adjusted under 35 U.S.C. 154(b) by 241 days.

(21) Appl. No.: 16/984,366

(22) Filed: Aug. 4, 2020

(65) Prior Publication Data

US 2021/0275705 A1 Sep. 9, 2021

Related U.S. Application Data

(60) Provisional application No. 63/019,534, filed on May 4, 2020, provisional application No. 62/984,360, filed on Mar. 3, 2020.

(51) Int. Cl.
*A61L 2/10* (2006.01)
*A61L 2/00* (2006.01)
*A61L 2/24* (2006.01)

(52) U.S. Cl.
CPC ............... *A61L 2/24* (2013.01); *A61L 2/0047* (2013.01); *A61L 2202/11* (2013.01); *A61L 2202/14* (2013.01)

(58) Field of Classification Search
CPC .................................... A61L 2/24; A61L 2/10
See application file for complete search history.

(56) References Cited

U.S. PATENT DOCUMENTS

| | | |
|---|---|---|
| 5,144,146 A | 9/1992 | Wekhof |
| 6,264,802 B1 | 7/2001 | Kamrukov et al. |
| 6,656,424 B1 | 12/2003 | Deal |
| 8,324,595 B2 | 12/2012 | Takahashi et al. |
| 9,039,966 B2 | 5/2015 | Anderson et al. |
| 9,289,523 B2 | 3/2016 | Lee |
| 9,839,706 B2 | 12/2017 | Anderson et al. |
| 9,937,274 B2 | 4/2018 | Clynne et al. |

(Continued)

FOREIGN PATENT DOCUMENTS

| | | |
|---|---|---|
| CN | 204745051 U | 11/2015 |
| CN | 207196113 U | 4/2018 |

(Continued)

OTHER PUBLICATIONS

CN108644662, English-language abstract.

(Continued)

*Primary Examiner* — Donald R Spamer
(74) *Attorney, Agent, or Firm* — Potomac Law Group, PLLC; Joseph F. Murphy

(57) ABSTRACT

A UVA/UVC system for reducing levels, on a surface, and inhibiting further growth of at least one pathogen on the surface, wherein the system has no deleterious effects on a human, in particular on a human eye or epidermis and dermis, wherein the system includes:
at least one UVA light source;
at least one UVC light source; and
at least one controller connected to each of the at least one UVA light source and the at least one UVC light source, for controlling at least one parameter of each of the UVA light source and UVC light source.

19 Claims, 5 Drawing Sheets

(56) References Cited

U.S. PATENT DOCUMENTS

| | | | |
|---|---|---|---|
| 9,981,052 | B2 | 5/2018 | Clynne et al. |
| 10,117,958 | B2 | 11/2018 | Dombrowsky et al. |
| 10,245,340 | B2 | 4/2019 | Stibich et al. |
| 10,245,341 | B2 | 4/2019 | Stibich et al. |
| 10,357,582 | B1 | 7/2019 | Barron et al. |
| 10,434,202 | B2 | 10/2019 | Hawkins et al. |
| 10,688,211 | B2 | 6/2020 | Barber, III |
| 2007/0053188 | A1 | 3/2007 | New et al. |
| 2009/0252646 | A1 | 10/2009 | Holden et al. |
| 2010/0096306 | A1 | 4/2010 | Chang |
| 2010/0246169 | A1 | 9/2010 | Anderson et al. |
| 2011/0243789 | A1 | 10/2011 | Roberts |
| 2012/0280147 | A1* | 11/2012 | Douglas .................. A61L 2/10 250/492.1 |
| 2013/0178921 | A1 | 7/2013 | Rogers |
| 2014/0241941 | A1 | 8/2014 | Kreitenberg |
| 2014/0322073 | A1 | 10/2014 | Link et al. |
| 2016/0339262 | A1 | 11/2016 | Fiset |
| 2017/0173195 | A1* | 6/2017 | Stibich .................. A61L 2/24 |
| 2017/0246331 | A1* | 8/2017 | Lloyd .................. A61Q 17/04 |
| 2017/0281811 | A1 | 10/2017 | Inskeep |
| 2018/0055959 | A1 | 3/2018 | Lin et al. |
| 2018/0182939 | A1 | 6/2018 | Liu et al. |
| 2018/0193502 | A1 | 7/2018 | Ufkes |
| 2018/0339073 | A1* | 11/2018 | Clynne .................. A61L 2/0047 |
| 2018/0369560 | A1* | 12/2018 | Ball .................. A61L 2/10 |
| 2019/0117811 | A1 | 4/2019 | Yoon et al. |
| 2019/0209722 | A1 | 7/2019 | Stibich et al. |
| 2020/0054893 | A1 | 2/2020 | Yoon et al. |
| 2020/0078482 | A1 | 3/2020 | Yoon et al. |

FOREIGN PATENT DOCUMENTS

| | | |
|---|---|---|
| CN | 108644662 A | 10/2018 |
| CN | 209092250 U | 7/2019 |
| CN | 111358977 A | 7/2020 |
| CN | 211096244 U | 7/2020 |
| CN | 111529727 A | 8/2020 |
| EP | 3287146 A1 | 2/2018 |
| JP | 200727553 A | 2/2007 |
| KR | 1020140112163 A | 9/2014 |
| KR | 1020160013504 A | 2/2016 |
| KR | 1020160070195 A | 6/2016 |
| KR | 1020160093832 A | 8/2016 |
| SG | 10201508854 A1 | 5/2016 |
| WO | 2007133537 A2 | 11/2007 |
| WO | 2010047479 A2 | 4/2010 |
| WO | 2011016679 A2 | 2/2011 |
| WO | 2016049143 A2 | 3/2016 |
| WO | 2018021595 A1 | 2/2018 |
| WO | 2018101943 A1 | 6/2018 |
| WO | 2019072205 A1 | 4/2019 |
| WO | 2020036471 A1 | 2/2020 |

OTHER PUBLICATIONS

CN204745051, English-language abstract.
CN207196113, English-language abstract.
CN209092250, English-language abstract.
JP2007027553, English-language abstract.
KR2014011263, English-language abstract.
KR20160013504, English-language abstract.
KR20160070195, English-language abstract.
KR20160093832, English-language abstract.
KR20180044536, English-language abstract.
WO2010/047479, English-language abstract on cover page.
WO2018/021595, English-language abstract on cover page.
Second Written Opinion of the International Preliminary Examining Authority for PCT/CA2021/050543 mailed May 5, 2022.
IES Photobiology Committee, "IES Committee Report: Germicidal Ultraviolet (GUV)-Frequently Asked Questions", Illuminating Engineering Society, May 5, 2020, pp. 1-24.
Ledrise LED Professional, "Disinfection with UV Light, >99% Kill Rate or Viruses (incl COVID-19) or Bacteria", https://www.ledrise.eu/blog/authors/ledrise-led-professional/), Jun. 16, 2021.
Fernandez, Sonia, "Ultraviolet LEDs prove effective in eliminating coronavirus from surfacesa and, potentially, air and water", Science Daily, Apr. 14, 2020, pp. 1-5.
Eickmann, Markus et al., "Inactivation of Ebola virus and Middle East respiratory syndrome coronavirus in platelet concentrates and plasma by ultraviolet C light and methylene blue plus visible light, respectively", Transfusion, 2018, vol. 00, pp. 1-6.
Razzaghi MD et al., "Role Low-Power Blue Laser With a Wavelength of 405 Nm in Increasing the Level of Nitric Oxide in Increasing the Resistance of Cells to the Virus (COVID-19) and its Effect on Virus (COVID-19) Mortality in Vitro", OSP Journal of Case Reports, Apr. 30, 2020, pp. 1-3.
Ackerman, Evan, "Autonomous Robots Are Helping Kill Coronavirus in Hospitals", https://spectrum.ieee.org/automation/robotics/medical-robots/autonomous-robots-are-helping-kill-coronavirus-in-hospitals.amp/html, Mar. 16, 2020.
Written Opinion of the International Preliminary Examining Authority issued in PCT/CA2020/051059 mailed Mar. 1, 2022.
English-language abstract of CN108644662.
English-language abstract of CN204745051.
English-language abstract of CN207196113.
English-language abstract of C209092250.
English-language abstract of JP2007027553.
English-language abstract of KR2014011263.
English-language abstract of KR20160013504.
English-language abstract of KR20160070195.
English-language abstract of KR20160093832.
English-language abstract of KR20180044536.
Xiao et al., Impact of UVA pre-radiation on UVC disinfection performance: Inactivation, repair and mechanism study Source, https://www.sciencedirect.com/science/article/abs/pii/S0043135418303890, Publication Date: May 15, 2018.
China GIL Tools, 9 LED Portable UVA+UVC Germicidal Lamp Anti-Bacterial Rate 99.9% Sanitizer UV Lamp for Home Cleaner Disinfection Bacteria, Microbes and Viruses Source: https://youlaite.en.made-in-china.com/product/sZLQqDcTntVy/China-9-LED-Portable-UVA-UVC-Germicidal-Lamp-Anti-Bacterial-Rate-99-9-Sanitizer-UV-Lamp-for-Home-Cleaner-Disinfection-Bacteria-Microbes-and-Viruses.html Publication Date: May 28, 2020.
Chevremont, Multivariate optimization of fecal bioindicator inactivation by coupling UV-A and UV-C LEDs Source: https://www.sciencedirect.com/science/article/abs/pii/S0011916411008678 Publication: Nov. 12, 2011.
International Search Report of PCT/CA2020/051059 dated Nov. 30, 2020.
Song, et al., Microorganisms inactivation by wavelength combinations of ultraviolet light-emitting diodes (UV-LEDS), Science of the Total Environment 665, (2019) 1103-1110.
Abstract of CN111358977A.
Abstract of CN2110966244U.
Abstract of CN111529727A.
Directive 2006/25/EC of the European Parliament and of the Council. Apr. 5, 2006.
American National Standard ANSI/IES RP-44-21 Recommended Practice: Ultraviolet Germicidal Irradiation (UVGI). Jul. 2021.
Office Action for Canadian Patent Application No. 3,172,386 issued on Nov. 21, 2023.
SeoulViosys. 3528-CUN0LF1B May 9, 2018.
Supplementary European Search Report for European Application No. 20922533.3 dated Mar. 14, 2024.
UCAR Center for Science Education. Ultraviolet (UV) Radiation. 2017.

* cited by examiner

COMBINATION ULTRA-VIOLET A (UVA) AND ULTRA-VIOLET C (UVC) SYSTEM FOR REDUCTION AND INHIBITION OF GROWTH OF PATHOGENS

FIELD OF THE DISCLOSURE

This disclosure relates to a system and method of reducing and inhibiting growth of pathogens, in public areas such as areas frequented by humans in public transit vehicles and the like, by the use of UVA and UVC light sources at levels detrimental to pathogens but safe for animals, including mammals and humans.

BACKGROUND

UVC light sources are known to be very effective in reducing bacteria levels on surfaces. However, the typical radiated power and exposure time needed to reduce the levels of bacteria may be deleterious to human eyes and epidermis and dermis layers.

There is a need for a system which will reduce the level of bacteria on a surface and inhibit further growth while being safe to human exposure.

SUMMARY

According to one aspect, there is provided an alternating UVA/UVC system for reducing and inhibiting further growth, on a surface, of at least one pathogen, wherein said system has no deleterious effects on an animal, including a human, in particular on a human eye or epidermis and dermis, wherein said system comprises:
  i) at least one UVA light source;
  ii) at least one UVC light source; and
  iii) at least one controller connected to each of said at least one UVA light source and said at least one UVC light source, for controlling at least one parameter of each of said UVA light source and UVC light source selected from light source, light intensity, radiated power level, wavelength, exposure time and combinations thereof: wherein said at least one UVC light source emits UVC light to a surface for a period of time reducing the level of said pathogen on said surface to a level that is safe to animals including humans, and said at least one UVA light source emits UVA light to a surface for a period of time inhibiting growth of said pathogen on said surface, such that during the time said at least one UVC light source and said at least one UVA light source is emitting on said surface, radiation levels from said at least one UVC light source and said at least one UVA light source is safe to animals, including humans; wherein when said at least one UVC light source is emitting UVA light to said surface, said at least one UVC light is off, and when said at least one UVA light source is emitting light to said surface, said at least one UVC light source is off: wherein cycling between said at least one UVC light source and said at least one UVA light source is controlled by said at least one controller.

According to one alternative, said at least one UVC light source has an operating wavelength of from about 275 nanometers (nm) to about 295 nm. In one alternative, said at least one UVC light source has an operating wavelength of about 275 nm.

According to one alternative, said at least one UVA light source has an operating wavelength of from about 385 nm to about 405 nm. In one alternative, said at least one UVA light source has an operating wavelength of about 405 nm.

According to yet another alternative, said at least one UVC light source is a light emitting diode (LED).

According to yet another alternative, said at least one UVA light source is a LED.

In one alternative, the at least one controller automatically cycles between emitting light from said at least one UVA light source and from said at least one UVC light source.

In one alternative, said at least one UVC light source has an emission at a power level and time duration to reduce pathogen levels on a surface exposed to said at least one UVC light source.

In one alternative, the power level is selected to ensure the radiated emission from said at least one UVC light source is at a safe level for human eyes and epidermis and dermis.

In one alternative, the time duration is selected to ensure the radiated emission from said at least one UVC light source is at a safe exposure time for human eyes and epidermis and dermis.

In one alternative, said at least one UVA light source has an emission at a power level to inhibit growth of at least one pathogen on a surface exposed to said at least one UVC light source, while safe for human eyes and epidermis and dermis, regardless of the exposure time.

In one alternative, said at least one UVC light source has a power rating of from about 10 mW to about 100 W. In one alternative, said at least one UVC light source has a power rating of 244 mW.

In one alternative, said at least one UVA light source has a power rating of from about 10 mW to about 100 W. In one alternative, said at least one UVA light source has a power rating of 20 mW.

In one alternative, said system reduces the level of pathogens on a surface exposed to said system by 1 to about 100%. In one alternative, by 10 to about 20%.

In yet another alternative, there is provided a method of reducing levels, on a surface, and inhibiting further growth of at least one pathogen, on said surface, wherein said method has no deleterious effects on an animal, including a human, in particular on a human eye or epidermis and dermis, wherein said method comprises:
  i) Exposing said surface to at least one UVC light source for a period of time to reduce the level of least one pathogen on said surface;
  ii) Terminating the exposure of the at least one UVC light source on said surface;
  iii) Exposing said UVC exposed surface to at least one UVA light source for a period of time to inhibit growth of least one pathogen on said surface;
  iv) Terminate the exposure of the at least one UVA light source on said surface;
  v) Optionally repeating steps i) to iv) in order to maintain a desired level of the least one pathogen, on said surface.

In one alternative, said at least one UVC light source has an operating wavelength of from about 275 nanometers (nm) to about 295 nm. In one alternative, said at least one UVC light source has an operating wavelength of about 275 nm.

According to one alternative, said at least one UVA light source has an operating wavelength of from about 385 nm to about 405 nm. In one alternative, said at least one UVA light source has an operating wavelength of about 405 nm.

According to yet another alternative, said at least one UVC light source is a light emitting diode (LED).

According to yet another alternative, said at least one UVA light source is a LED.

In one alternative, steps i) to iv) are controlled by at least one controller automatically cycling between emitting light from said at least one UVA light source and from said at least one UVC light source.

In one alternative, said at least one UVC light source has an emission at a power level and time duration to reduce at least one pathogen on a surface exposed to said at least one UVC light source.

In one alternative, the power level is selected to ensure the radiated emission from said at least one UVC light source is at a safe level for human eyes and epidermis and dermis.

In one alternative, the time duration is selected to ensure the radiated emission from said at least one UVC light source is at a safe exposure time for human eyes and epidermis and dermis.

In one alternative, said at least one UVA light source has an emission at a power level to inhibit growth of at least one pathogen on a surface exposed to said at least one UVC light source, while safe for human eyes and epidermis and dermis, regardless of the exposure time.

In one alternative, said at least one UVC light source has a power rating of from about 10 mW to about 100 W. In one alternative, said at least one UVC light source has a power rating of 244 mW.

In one alternative, said at least one UVA light source has a power rating of from about 10 mW to about 100 W. In one alternative, said at least one UVA light source has a power rating of 20 mW.

In one alternative, said method reduces the level, and in another alternative inhibits growth, of at least one pathogen on a surface by 1 to 100%. In one alternative, by at least one of the following ranges: 10 to 20%, 20 to 30%, 30 to 40%, 40 to 50%, 50 to 60%, 60 to 70%, 70 to 80%, 80 to 90% and 90 to 100%.

In one alternative, said method includes a UVC time interval of UVC on from 1 sec to 300 sec (wherein the UVA would be off), and a UVA on from 1 h to 10 days (wherein the UVC would be off). The UVC on/off UVA on/off time intervals will depend on factor such as: power rating of the UV light source: pathogens targeted; location of pathogens: levels of pathogens: type of pathogens.

In one alternative, the UVA light source may remain on at levels safe to animals including humans to inhibit pathogen growth and UVC is turned on at intervals to reduce pathogen levels should pathogen growth inhibition meet its limit, if any.

Herein the term pathogen may include bacteria, viruses, yeast, protozoa, mould and combinations thereof.

In one alternative, said pathogen is selected from the group consisting of *E. Coli* K12. *S. Epidermidis* and *B. Subtilis*.

Herein the term surface includes surfaces typically found in public places such as bathrooms and kitchens, including but not limited to countertops, hard counters, wood counters, concrete, plastic, rubber, leather, material and the like.

DETAILED DESCRIPTION

Figure 1:
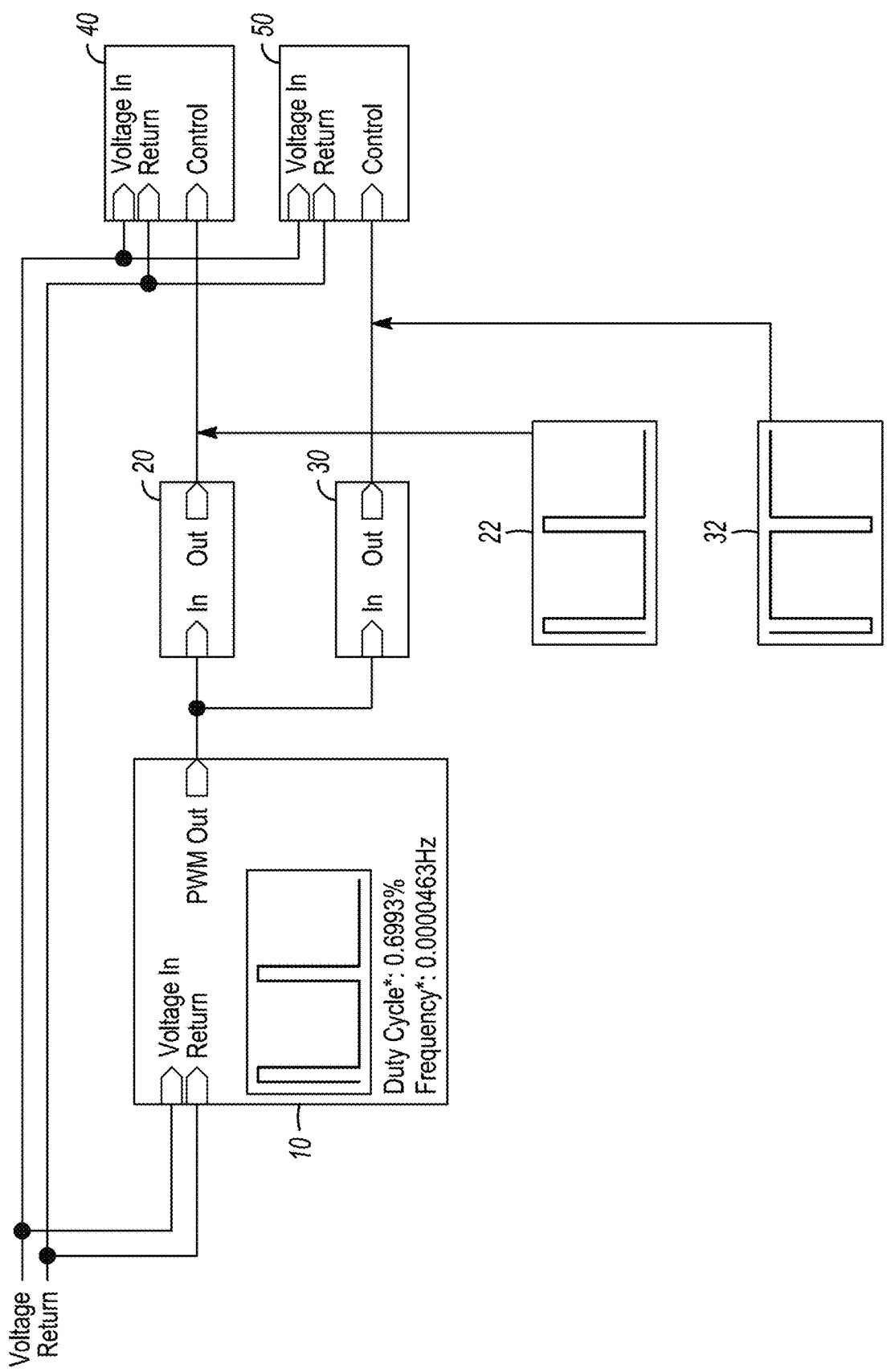
FIG. 1 is a block diagram of the system, according to one alternative.

Referring now to FIG. 1, there is depicted a block diagram of a single Pulse Width Modulation (PWM) example for the system described herein. A PWM generator 10 generates a single continuous PWM which feeds into two circuits. Here the duty cycle of 0.6993% and frequency of 0.0000463 Hz are set to achieve a positive logic output for a duration of 150 seconds every 6 hours. The first circuit is an optional logic buffer circuit 20 for controlling the pulsing of the UVC emitter 40. The logic buffer circuit 20 ensures that the UVC emitter 40 is emitting when the PWM generator 10 is outputting a high logic level, and off when the PWM generator 10 is outputting a low logic level. See the output curve 22 (the PWM output duty cycle is maintained for the entry into this circuit, the light source will be on for the short pulse). The second circuit is a logic inverter 30 controlling the UVA emitter 50, ensuring that the UVA emitter is off when the PWM generator 10 is outputting a high logic level, and UVA emitter is on when the PWM generator 10 is outputting a low logic level. See the inverted output curve 32 (the PWM output duty cycle is inverted for the entry into this circuit, the light source will be on for the long pulse).

Figure 2:
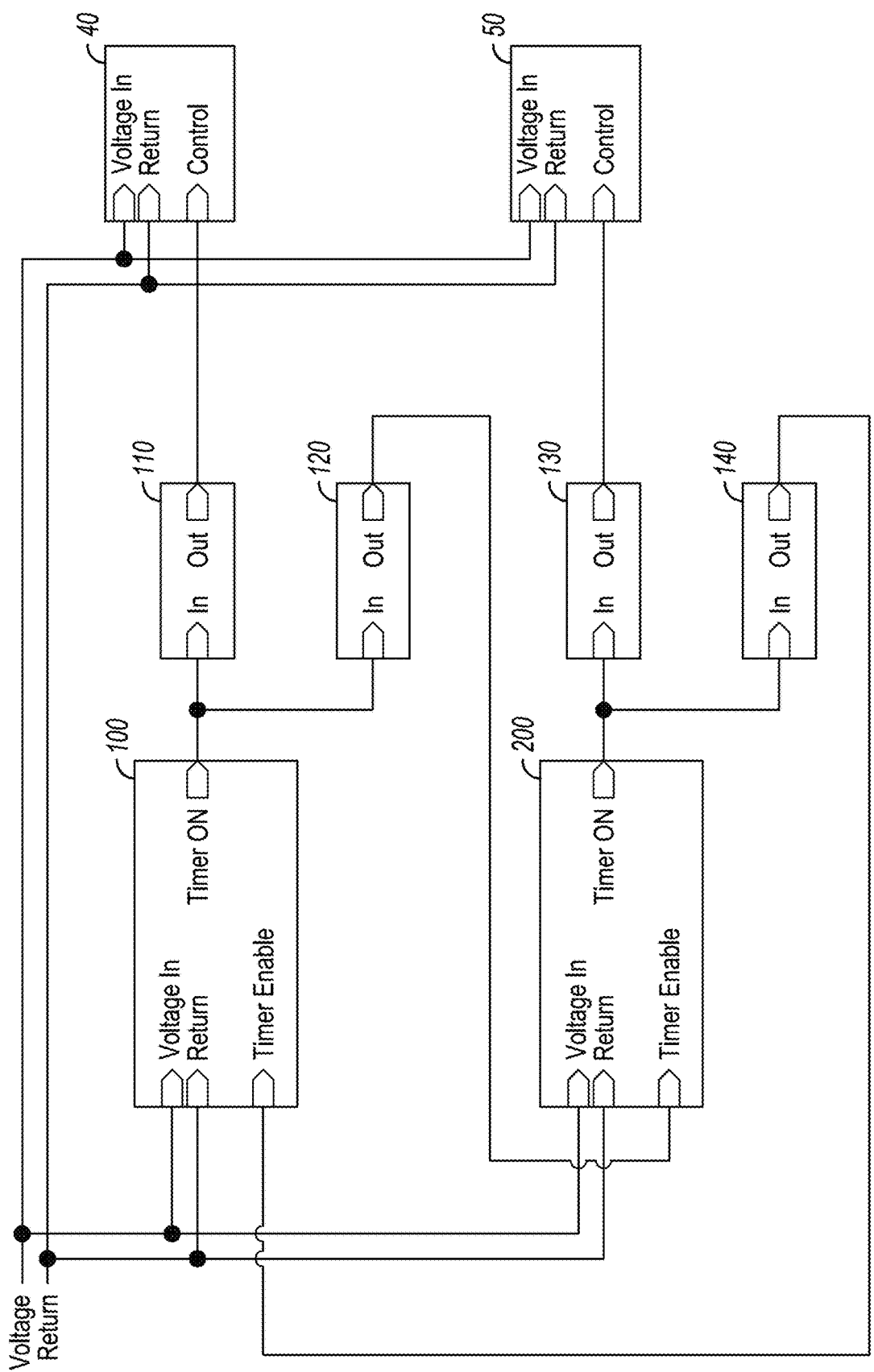
FIG. 2 is a block diagram of the system, according to another alternative.

Referring now to FIG. 2, there is depicted a block diagram of a timer controlled system, according to one alternative. In this example, there is a UVC timer circuit 100 and a UVA timer circuit 200 each controlling the UVC emitter 40 and UVA emitter 50 respectively. The UVC timer circuit 100 is set for 150 seconds on and the UVA timer circuit 200 is set for 6 hours. During start up, the UVC timer circuit 100 is enabled and outputs a logic high which is fed into a first logic buffer 110 and first logic inverter 120. The first logic buffer 110 controls the UVC emitter 40 to be on, while the first logic inverter 120 is used to ensure the UVA timer circuit 200 is off. Once the UVC timer circuit 100 completes the 150 seconds, the output changes state to turn off the UVC emitter 40 and turn on the UVA timer circuit 200 for 6 hours. Once enabled, UVA timer circuit 200 outputs a logic high which is fed into a second logic buffer 130 and second logic inverter 140. The second logic buffer 130 controls the UVA emitter 50 to be on, while the second logic inverter 140 is used to ensure the UVC timer circuit 100 is off. Once the 6 hours is completed, the output changes state to turn off the UVA emitter 50 and turn on the UVC timer circuit 100 which turns on the UVC emitter 40 for 150 seconds, and the cycle repeats as required. The time value of each time will be determined by a variety of factors including pathogen to be eliminated, power level of UV light source, size of room, etc.

Example 1

UVC LED ALONE Reduction Study

FLS UV Tool program was used to calculate the effect of UVC LEDS on reducing bacteria levels in an enclosed space measuring 3 metres×3 metres×3 metres. Nine (9) UVC LEDs each having a wavelength of 275 nm and a power rating of 244.2 mW were tested for 20% bacteria reduction and safety to human eyes and skin at various distances (floor level, 2 meters above floor level) from the light source on the ceiling (3 metres from the floor) of the enclosed space.

Each UVC LED was placed on the ceiling of the room in an equidistant manner from each other resulting in a 3×3 array of UVC LEDs and each UVC LED having a radiating angle of light source of 135° (FWHM*).

*The LED beam angle, or LED viewing angle as it is also commonly referred, measures the usable light emitted from an LED source. In most common situations, one of two methods is used to define the beam angle: the first looks for the angle at which 50% of the peak intensity is reached on either side of the origin. The second looks for the angle at which 10% of the peak intensity is reached on each side of the origin. Most commonly used is the Full Width, Half Maximum (FWHM) relating to 50% intensity, if for example an LED was measured to have 50% intensity at 15° it's viewing angle (FWHM) would be 30°.

The following pathogens were tested with the amount of time required for the UVC to be on for 20% reduction in levels at floor level (i.e. 3 metres from light source) based on the above parameters:

| | |
|---|---|
| Bacillus anthracis-Anthrax | 1 m 42 s |
| Bacillus anthracis spores-Anthrax spores | 9 m 3 s |
| Bacillus magaterium sp. (spores) | 1 m 1 s |
| Bacillus magaterium sp. (veg.) | 29.41 s |
| Bacillus paratyphusus | 1 m 11 s |
| Bacillus subtilis spores | 4 m 18 s |
| Bacillus subtilis | 2 m 9 s |
| Clostridium difficile | 4 m 18 s |
| Corynebacterium diphtheriae | 1 m 16 s |
| Ebertelia typhosa | 48.23 s |
| Escherichia coli | 1 m 17 s |
| Leptospiracanicola-infectious Jaundice | 1 m 10 s |
| Microccocus candidus | 2 m 24 s |
| Microccocus sphaeroides | 3 m 1 s |
| Mycobacterium tuberculosis | 1 m 57 s |
| Neisseria catarrhalis | 1 m 39 s |
| Phytomonas tumefaciens | 1 m 34 s |
| Proteus vulgaris | 1 m 17 s |
| Pseudomonas aeruginosa | 2 m 3 s |
| Pseudomonas fluorescens | 1 m 17 s |
| Salmonella enteritidis | 1 m 29 s |
| Salmonela paratyphi-Enteric fever | 1 m 11 s |
| Salmonella typhosa-Typhoid fever | 48.23 s |
| Salmonella typhimurium | 2 m 58 s |
| Sarcina lutea | 5 m 10 s |
| Serratia marcescens | 1 m 12 s |
| Shigella dyseteriae-Dysentery | 49.41 s |
| Shigella flexneri-Dysentery | 39.99 s |
| Shigella paradysenteriae | 39.99 s |
| Spirillum rubrum | 1 m 12 s |
| Staphylococcus albus | 1 m 7 s |
| Staphylococcus aureus | 1 m 17 s |
| Staphylococcus hemolyticus | 1 m 4 s |
| Staphylococcus lactis | 1 m 43 s |
| Streptococcus viridans | 44.70 s |
| Virus | |
| Bacteriopfage-E. Coli | 1 m 17 s |
| Infectious Hepatitis | 1 m 34 s |
| Influenza | 1 m 17 s |
| Poliovirus-Poliomyelitis | 1 m 17 s |
| Yeast | |
| Brewers yeast | 1 m 17 s |
| Candida albicans | 2 m 29 s |
| Common yeast cake | 2 m 35 s |
| Saccharomyces carevisiae | 2 m 35 s |
| Saccharomyces ellipsoideus | 2 m 35 s |
| Saccharomyces spores | 3 m 27 s |

UVC alone required 9 minutes and 3 seconds to reduce all bacteria by 20%.

Human safety levels maximum exposure time were also measured at 1 metre from light source for wavelengths that include the UVC LED wavelength studied.

| Wavelength | Maximum Time |
|---|---|
| 180-400 nm | 3 m 31 s |
| 300-700 nm | No Limit |
| 300-700 nm | No Limit |
| 180-280 nm | 3 m 26 s |
| 280-302 nm | 34 m 15 s |
| 303 nm | >8 h |
| 304 nm | >8 h |
| 305 nm | >8 h |

The UVC LED ONLY study shows for reduction of the bacteria levels by 20% requires 9 mins and 3 secs which would exceed the maximum safe time of 3 minutes and 26 secs above.

Example 2

UVA LED ONLY Reduction Study

Nine (9) UVA LEDs each having a wavelength of 405 nm and a power rating of 1000 mW were tested for reducing bacteria growth at levels safe to human eyes and skin at various distances (floor level, 1 meter above floor level, 2 meters above floor level) from the light source in a test room size of 3 metres by 3 metres by 3 metres for a duration of 40 hours.

Each UVA LED was placed on the ceiling of the room in an equidistant manner from each other resulting in a 3×3 array of UVA LEDs and each UVA LED having a radiating angle of light source of 120° (full width half max).

The pathogens of study 1 were used for this study as well.

Pathogens were inhibited as follows using the UVA LED described above:

| | % Reduction at system dosage | 20.00% reduction time required |
|---|---|---|
| Bacteria | | |
| Bacillus anthracis-Anthrax | 69.40% | 7 h 35 m 46 s |
| Bacillus anthracis spores-Anthrax spores | 19.99% | >24 h |
| Bacillus magaterium sp. (spores) | 86.21% | 4 h 32 m 24 s |
| Bacillus magaterium sp. (veg.) | 98.38% | 2 h 10 m 58 s |
| Bacillus paratyphusus | 81.53% | 5 h 19 m 33 s |
| Bacillus subtilis spores | 37.39% | 19 h 12 m 31 s |
| Bacillus subtilis | 60.80% | 9 h 36 m 15 s |
| Clostridium difficile | 37.39% | 19 h 12 m 31 s |
| Corynebacterium diphtheriae | 79.46% | 5 h 41 m 2 s |
| Ebertelia typhosa | 91.90% | 3 h 34 m 47 s |
| Escherichia coli | 79.01% | 5 h 45 m 45 s |
| Leptospiracanicola-infectious Jaundice | 82.04% | 5 h 14 m 19 s |
| Microccocus candidus | 56.73% | 10 h 44 m 21 s |
| Microccocus sphaeroides | 48.78% | 13 h 26 m 45 s |
| Mycobacterium tuberculosis | 64.31% | 8 h 43 m 52 s |
| Neisseria catarrhalis | 70.24% | 7 h 25 m 17 s |
| Phytomonas tumefaciens | 72.41% | 6 h 59 m 5 s |
| Proteus vulgaris | 94.84% | 3 h 2 m 6 s |
| Pseudomonas aeruginosa | 87.93% | 4 h 15 m 18 s |
| Pseudomonas fluorescens | 79.01% | 5 h 45 m 45 s |
| Salmonella enteritidis | 74.22% | 6 h 38 m 8 s |
| Salmonela paratyphi-Enteric fever | 81.53% | 5 h 19 m 33 s |
| Salmonella typhosa-Typhoid fever | 91.90% | 3 h 34 m 47 s |
| Salmonella typhimurium | 49.23% | 13 h 16 m 17 s |
| Sarcina lutea | 32.31% | 23 h 3 m 1 s |
| Serratia marcescens | 81.22% | 5 h 22 m 42 s |
| Shigella dyseteriae-Dysentery | 91.40% | 3 h 40 m 1 s |

-continued

| | % Reduction at system dosage | 20.00% reduction time required |
|---|---|---|
| *Shigella flexneri*-Dysentery | 95.17% | 2 h 58 m 6 s |
| *Shigella paradysenteriae* | 95.17% | 2 h 58 m 6 s |
| *Spirillum rubrum* | 81.22% | 5 h 22 m 42 s |
| *Staphylococcus albus* | 83.49% | 4 h 59 m 39 s |
| *Staphylococcus aureus* | 100.00% | 42 m 50 s |
| *Staphylococcus hemolyticus* | 84.64% | 4 h 48 m 7 s |
| *Staphylococcus lactis* | 68.99% | 7 h 41 m 0 s |
| *Streptococcus viridans* | 93.35% | 3 h 19 m 4 s |
| *Vibrio comma*-Cholera | 79.51% | 5 h 40 m 31 s |

The amount of time required to reduce by 20% is at least 23 hours.

Safety level were measured at 1 metre from light source.

| Wavelength | Maximum Limit (at conditions in UV Tool tab) | Limit Units | Average | Peak | SAFE? | Maximum Time |
|---|---|---|---|---|---|---|
| 180-400 nm | 3 | mJ/cm^2 | 5.38 | 7.45 | UNSAFE | >8 h |
| 300-700 nm | 0.001 | mW/cm^2 | 0.02 | 0.02 | UNSAFE | 7 m 45 s |
| 300-700 nm | 10.000 | mW/cm^2 sr | 1.55 | 2.15 | SAFE | No Limit |
| 180-280 nm | 3 | mJ/cm^2 | 3.61 | 5.00 | UNSAFE | >8 h |
| 280-302 nm | 3 | mJ/cm^2 | 4.32 | 5.98 | UNSAFE | >8 h |
| 303 nm | 4 | mJ/cm^2 | 0.14 | 0.20 | SAFE | >8 h |
| 304 nm | 6 | mJ/cm^2 | 0.21 | 0.30 | SAFE | >8 h |
| 305 nm | 10 | mJ/cm^2 | 0.21 | 0.29 | SAFE | >8 h |
| 306 nm | 16 | mJ/cm^2 | 0.05 | 0.06 | SAFE | >8 h |
| 307 nm | 25 | mJ/cm^2 | 0.23 | 0.31 | SAFE | >8 h |
| 308 nm | 40 | mJ/cm^2 | 0.14 | 0.19 | SAFE | >8 h |
| 309 nm | 63 | mJ/cm^2 | 0.22 | 0.31 | SAFE | >8 h |
| 310 nm | 100 | mJ/cm^2 | 0.20 | 0.27 | SAFE | >8 h |
| 311 nm | 160 | mJ/cm^2 | 0.20 | 0.27 | SAFE | >8 h |
| 312 nm | 250 | mJ/cm^2 | 0.24 | 0.33 | SAFE | >8 h |
| 313 nm | 400 | mJ/cm^2 | 0.28 | 0.39 | SAFE | >8 h |
| 314 nm | 630 | mJ/cm^2 | 0.21 | 0.29 | SAFE | >8 h |
| 315-400 nm | 1000 | mJ/cm^2 | 2854.85 | 3952.39 | UNSAFE | >8 h |

UVA alone for reduction exceeds safety limits at 7 min and 45 secs.

Example 3

UVC Pulse Study

FLS UV tool software program was used to calculate the effect of UVC LEDS in a pulsing fashion (on for a period of time, off for a period of time) on reducing bacteria levels in an enclosed space measuring 3 metres×3 metres×3 metres. Nine (9) UVC LEDs each having a UVC wavelength of 275 nm and a power rating of 244.2 mW were tested for 20% bacteria reduction and safety to human eyes and skin at various distances (floor level, 2 meters above floor level) from the light source on the ceiling (3 metres from the floor) of the enclosed space.

Each UVC LED was placed on the ceiling of the room in an equidistant manner from each other resulting in a 3×3 array of UVC LEDs and each UVC LED having a radiating angle of light source of 135° (FWHM) and pulsed on for 150 sec at a time and pathogen levels were measured. Then the time required for 20% reduction was calculated based on the % reduction at 150 secs.

| Bacteria | % reduction at 150 secs | Time required for 20% reduction |
|---|---|---|
| *Bacillus anthracis*-Anthrax | 27.90% | 1 m 42 s |
| *Bacillus anthracis* spores-Anthrax spores | 5.97% | 9 m 3 s |
| *Bacillus magaterium* sp. (spores) | 42.14% | 1 m 1 s |
| *Bacillus magaterium* sp. (veg.) | 67.96% | 29.41 s |
| *Bacillus paratyphusus* | 37.28% | 1 m 11 s |
| *Bacillus subtilis* spores | 12.13% | 4 m 18 s |
| *Bacillus subtilis* | 22.79% | 2 m 9 s |
| *Clostridium difficile* | 12.13% | 4 m 18 s |
| *Corynebacterium diphtheriae* | 35.41% | 1 m 16 s |
| *Ebertelia typhosa* | 50.04% | 48.23 s |
| *Escherichia coli* | 35.02% | 1 m 17 s |
| *Leptospiracanicola*-infectious Jaundice | 37.76% | 1 m 10 s |

-continued

| | % reduction at 150 secs | Time required for 20% reduction |
|---|---|---|
| *Microccocus candidus* | 20.65% | 2 m 24 s |
| *Microccocus sphaeroides* | 16.87% | 3 m 1 s |
| *Mycobacterium tuberculosis* | 24.76% | 1 m 57 s |
| *Neisseria catarrhalis* | 28.45% | 1 m 39 s |
| *Phytomonas tumefaciens* | 29.93% | 1 m 34 s |
| *Proteus vulgaris* | 35.02% | 1 m 17 s |
| *Pseudomonas aeruginosa* | 23.74% | 2 m 3 s |
| *Pseudomonas fluorescens* | 35.02% | 1 m 17 s |
| *Salmonella enteritidis* | 31.23% | 1 m 29 s |
| *Salmonela paratyphi*-Enteric fever | 37.28% | 1 m 11 s |
| *Salmonella typhosa*-Typhoid fever | 50.04% | 48.23 s |
| *Salmonella typhimurium* | 17.07% | 2 m 58 s |
| *Sarcina lutea* | 10.22% | 5 m 10 s |
| *Serratia marcescens* | 36.99% | 1 m 12 s |
| *Shigella dyseteriae*-Dysentery | 49.21% | 49.41 s |
| *Shigella flexneri*-Dysentery | 56.69% | 39.99 s |
| *Shigella paradysenteriae* | 56.69% | 39.99 s |
| *Spirillum rubrum* | 36.99% | 1 m 12 s |
| *Staphylococcus albus* | 39.19% | 1 m 7 s |
| *Staphylococcus aureus* | 35.02% | 1 m 17 s |
| *Staphylococcus hemolyticus* | 40.39% | 1 m 4 s |
| *Staphylococcus lactis* | 27.63% | 1 m 43 s |
| *Streptococcus viridans* | 52.71% | 44.70 s |
| *Vibrio comma*-Cholera | 35.45% | 1 m 16 s |

-continued

|  | % reduction at 150 secs | Time required for 20% reduction |
|---|---|---|
| Virus | | |
| Bacteriopfage-*E. Coli* | 35.02% | 1 m 17 s |
| Infectious Hepatitis | 29.93% | 1 m 34 s |
| Influenza | 35.02% | 1 m 17 s |
| Poliovirus-Poliomyelitis | 35.02% | 1 m 17 s |
| Yeast | | |
| Brewers yeast | 35.02% | 1 m 17 s |
| *Candida albicans* | 20.05% | 2 m 29 s |
| Common yeast cake | 19.39% | 2 m 35 s |
| *Saccharomyces carevisiae* | 19.39% | 2 m 35 s |
| *Saccharomyces ellipsoideus* | 19.39% | 2 m 35 s |
| *Saccharomyces* spores | 14.93% | 3 m 27 s |

Safety levels were measured at 1 metre from light source.

| Wavelength | Maximum Limit | Limit Units | Average | Peak | SAFE? | Maximum Time |
|---|---|---|---|---|---|---|
| 180-400 nm | 3 | mJ/cm^2 | 1.54322 | 2.12407 | SAFE | 3 m 31 s |
| 300-700 nm | 0.067 | mW/cm^2 | 0.00003 | 0.00005 | SAFE | No Limit |
| 300-700 nm | 666.667 | mW/cm^2 sr | 0.00330 | 0.00455 | SAFE | No Limit |
| 180-280 nm | 3 | mJ/cm^2 | 1.58233 | 2.17791 | SAFE | 3 m 26 s |
| 280-302 nm | 3 | mJ/cm^2 | 0.15908 | 0.21896 | SAFE | 34 m 15 s |
| 303 nm | 4 | mJ/cm^2 | 0.00068 | 0.00093 | SAFE | >8 h |
| 304 nm | 6 | mJ/cm^2 | 0.00069 | 0.00095 | SAFE | >8 h |
| 305 nm | 10 | mJ/cm^2 | 0.00053 | 0.00073 | SAFE | >8 h |
| 306 nm | 16 | mJ/cm^2 | 0.00049 | 0.00067 | SAFE | >8 h |
| 307 nm | 25 | mJ/cm^2 | 0.00050 | 0.00069 | SAFE | >8 h |
| 308 nm | 40 | mJ/cm^2 | 0.00046 | 0.00063 | SAFE | >8 h |
| 309 nm | 63 | mJ/cm^2 | 0.00044 | 0.00060 | SAFE | >8 h |
| 310 nm | 100 | mJ/cm^2 | 0.00041 | 0.00057 | SAFE | >8 h |
| 311 nm | 160 | mJ/cm^2 | 0.00037 | 0.00051 | SAFE | >8 h |
| 312 nm | 250 | mJ/cm^2 | 0.00036 | 0.00050 | SAFE | >8 h |
| 313 nm | 400 | mJ/cm^2 | 0.00028 | 0.00038 | SAFE | >8 h |
| 314 nm | 630 | mJ/cm^2 | 0.00031 | 0.00043 | SAFE | >8 h |
| 315-400 nm | 1000 | mJ/cm^2 | 0.00847 | 0.01166 | SAFE | >8 h |

For the above, pulsing UVC on at 150 sec intervals would keep within the safety limits and meet the 20% reduction levels.

Example 4

UVA for Growth Inhibition after UVC Pulsing

FLS UV tool software program was used to calculate the effect of UVA LEDS in a pulsing fashion (on for a period of time, off for a period of time) on inhibiting bacteria levels in an enclosed space measuring 3 metres×3 metres×3 metres after exposure to UVC as per example 3 above. Nine (9) UVC LEDs each having a UVA wavelength of 405 nm and a power rating of 20 mW were tested for growth inhibition and safety to human eyes and skin at various distances (floor level, 2 meters above floor level) from the light source on the ceiling (3 metres from the floor) of the enclosed space.

Each UVA LED was placed on the ceiling of the room in an equidistant manner from each other resulting in a 3×3 array of UVA LEDs and each UVA LED having a radiating angle of light source of 120° (FWHM) and pulsed on for 6 hours at a time (alternating with UVC pulsing) and pathogen levels were measured.

|  | Pathogen Level |
|---|---|
| Bacteria | |
| *Bacillus anthracis*-Anthrax | 0.35% |
| *Bacillus anthracis* spores-Anthrax spores | 0.07% |
| *Bacillus magaterium* sp. (spores) | 0.59% |
| *Bacillus magaterium* sp. (veg.) | 1.22% |
| *Bacillus paratyphusus* | 0.50% |
| *Bacillus subtilis* spores | 0.14% |
| *Bacillus subtilis* | 0.28% |
| *Clostridium difficile* | 0.14% |
| *Corynebacterium diphtheriae* | 0.47% |
| *Ebertelia typhosa* | 0.75% |
| *Escherichia coli* | 0.46% |
| *Leptospiracanicola*-infectious Jaundice | 0.51% |
| *Microccocus candidus* | 0.25% |
| *Microccocus sphaeroides* | 0.20% |
| *Mycobacterium tuberculosis* | 0.31% |
| *Neisseria catarrhalis* | 0.36% |

-continued

|  | Pathogen Level |
|---|---|
| *Phytomonas tumefaciens* | 0.38% |
| *Proteus vulgaris* | 0.88% |
| *Pseudomonas aeruginosa* | 0.63% |
| *Pseudomonas fluorescens* | 0.46% |
| *Salmonella enteritidis* | 0.40% |
| *Salmonela paratyphi*-Enteric fever | 0.50% |
| *Salmonella typhosa*-Typhoid fever | 0.75% |
| *Salmonella typhimurium* | 0.20% |
| *Sarcina lutea* | 0.12% |
| *Serratia marcescens* | 0.50% |
| *Shigella dyseteriae*-Dysentery | 0.73% |
| *Shigella flexneri*-Dysentery | 0.90% |
| *Shigella paradysenteriae* | 0.90% |
| *Spirillum rubrum* | 0.50% |
| *Staphylococcus albus* | 0.53% |
| *Staphylococcus aureus* | 3.68% |
| *Staphylococcus hemolyticus* | 0.56% |
| *Staphylococcus lactis* | 0.35% |
| *Streptococcus viridans* | 0.80% |
| *Vibrio comma*-Cholera | 0.47% |
| Virus | |
| Bacteriopfage-*E. Coli* | 0.46% |
| Infectious Hepatitis | 0.38% |
| Influenza | 0.46% |
| Poliovirus-Poliomyelitis | 0.46% |

| Pathogen Level | |
| --- | --- |
| Yeast | |
| Brewers yeast | 0.46% |
| *Candida albicans* | 0.24% |
| Common yeast cake | 0.23% |
| *Saccharomyces carevisiae* | 0.23% |
| *Saccharomyces ellipsoideus* | 0.23% |
| *Saccharomyces spores* | 0.17% |

Growth of the above bacteria was inhibited using UVA. Safety levels at 1 metre below light source was:

| Wavelength | Maximum Limit | Limit Units | Average | Peak | SAFE? | Maximum Time |
| --- | --- | --- | --- | --- | --- | --- |
| 180-400 nm | 3 | mJ/cm^2 | 0.01601 | 0.02217 | SAFE | >240 h |
| 300-700 nm | 0.001 | mW/cm^2 | 0.00031 | 0.00043 | SAFE | No Limit |
| 300-700 nm | 10.000 | mW/cm^2 sr | 0.03106 | 0.04300 | SAFE | No Limit |
| 315-400 nm | 1000 | mJ/cm^2 | 8.49816 | 11.76525 | SAFE | >240 h |

Safety levels were not exceeded while maintaining growth inhibition with UVA/UVC combination.

The following table shows levels of Anthrax Spores on a surface of a 3×3×3 metre room as per the above conditions with UVC pulsing on/off and UVA pulsing on/off using the conditions of Examples 3 and 4.

| Each pulse is 0.041677 h | Time in hours | UVC | UVA | % Level of Anthrax Spores on Surface |
| --- | --- | --- | --- | --- |
| 0.0 | 0.041667 | ON | OFF | 100 |
| 0.041667 | 0.083333 | OFF | ON | 94.03 |
| 0.041667 | 0.125 | OFF | ON | 94.03 |
| 0.041667 | 0.166667 | OFF | ON | 94.03 |
| 0.041667 | 0.208333 | OFF | ON | 94.03 |
| 0.041667 | 0.25 | OFF | ON | 94.03 |
| 0.041667 | 0.291667 | OFF | ON | 94.03 |
| 0.041667 | 0.333333 | OFF | ON | 94.03 |
| 0.041667 | 0.375 | OFF | ON | 94.03 |
| 0.041667 | 0.416667 | OFF | ON | 94.03 |
| 0.041667 | 0.458333 | OFF | ON | 94.03 |
| 0.041667 | 0.5 | OFF | ON | 94.03 |
| 0.041667 | 0.541667 | OFF | ON | 94.03 |
| 0.041667 | 0.583333 | OFF | ON | 94.03 |
| 0.041667 | 0.625 | OFF | ON | 94.03 |
| 0.041667 | 0.666667 | OFF | ON | 94.03 |
| 0.041667 | 0.708333 | OFF | ON | 94.03 |
| 0.041667 | 0.75 | OFF | ON | 94.03 |
| 0.041667 | 0.791667 | OFF | ON | 94.03 |
| 0.041667 | 0.833333 | OFF | ON | 94.03 |
| 0.041667 | 0.875 | OFF | ON | 94.03 |
| 0.041667 | 0.916667 | OFF | ON | 94.03 |
| 0.041667 | 0.958333 | OFF | ON | 94.03 |
| 0.041667 | 1 | OFF | ON | 94.03 |
| 0.041667 | 1.041667 | OFF | ON | 94.03 |
| 0.041667 | 1.083333 | OFF | ON | 94.03 |
| 0.041667 | 1.125 | OFF | ON | 94.03 |
| 0.041667 | 1.166667 | OFF | ON | 94.03 |
| 0.041667 | 1.208333 | OFF | ON | 94.03 |
| 0.041667 | 1.25 | OFF | ON | 94.03 |
| 0.041667 | 1.291667 | OFF | ON | 94.03 |
| 0.041667 | 1.333333 | OFF | ON | 94.03 |
| 0.041667 | 1.375 | OFF | ON | 94.03 |
| 0.041667 | 1.416667 | OFF | ON | 94.03 |
| 0.041667 | 1.458333 | OFF | ON | 94.03 |
| 0.041667 | 1.5 | OFF | ON | 94.03 |
| 0.041667 | 1.541667 | OFF | ON | 94.03 |
| 0.041667 | 1.583333 | OFF | ON | 94.03 |
| 0.041667 | 1.625 | OFF | ON | 94.03 |
| 0.041667 | 1.666667 | OFF | ON | 94.03 |
| 0.041667 | 1.708333 | OFF | ON | 94.03 |
| 0.041667 | 1.75 | OFF | ON | 94.03 |
| 0.041667 | 1.791667 | OFF | ON | 94.03 |
| 0.041667 | 1.833333 | OFF | ON | 94.03 |
| 0.041667 | 1.875 | OFF | ON | 94.03 |
| 0.041667 | 1.916667 | OFF | ON | 94.03 |
| 0.041667 | 1.958333 | OFF | ON | 94.03 |
| 0.041667 | 2 | OFF | ON | 94.03 |
| 0.041667 | 2.041667 | OFF | ON | 94.03 |
| 0.041667 | 2.083333 | OFF | ON | 94.03 |
| 0.041667 | 2.125 | OFF | ON | 94.03 |
| 0.041667 | 2.166667 | OFF | ON | 94.03 |
| 0.041667 | 2.208333 | OFF | ON | 94.03 |
| 0.041667 | 2.25 | OFF | ON | 94.03 |
| 0.041667 | 2.291667 | OFF | ON | 94.03 |
| 0.041667 | 2.333333 | OFF | ON | 94.03 |
| 0.041667 | 2.375 | OFF | ON | 94.03 |
| 0.041667 | 2.416667 | OFF | ON | 94.03 |
| 0.041667 | 2.458333 | OFF | ON | 94.03 |
| 0.041667 | 2.5 | OFF | ON | 94.03 |
| 0.041667 | 2.541667 | OFF | ON | 94.03 |
| 0.041667 | 2.583333 | OFF | ON | 94.03 |
| 0.041667 | 2.625 | OFF | ON | 94.03 |
| 0.041667 | 2.666667 | OFF | ON | 94.03 |
| 0.041667 | 2.708333 | OFF | ON | 94.03 |
| 0.041667 | 2.75 | OFF | ON | 94.03 |
| 0.041667 | 2.791667 | OFF | ON | 94.03 |
| 0.041667 | 2.833333 | OFF | ON | 94.03 |
| 0.041667 | 2.875 | OFF | ON | 94.03 |
| 0.041667 | 2.916667 | OFF | ON | 94.03 |
| 0.041667 | 2.958333 | OFF | ON | 94.03 |
| 0.041667 | 3 | OFF | ON | 94.03 |
| 0.041667 | 3.041667 | OFF | ON | 94.03 |
| 0.041667 | 3.083333 | OFF | ON | 94.03 |
| 0.041667 | 3.125 | OFF | ON | 94.03 |
| 0.041667 | 3.166667 | OFF | ON | 94.03 |
| 0.041667 | 3.208333 | OFF | ON | 94.03 |
| 0.041667 | 3.25 | OFF | ON | 94.03 |
| 0.041667 | 3.291667 | OFF | ON | 94.03 |
| 0.041667 | 3.333333 | OFF | ON | 94.03 |
| 0.041667 | 3.375 | OFF | ON | 94.03 |
| 0.041667 | 3.416667 | OFF | ON | 94.03 |
| 0.041667 | 3.458333 | OFF | ON | 94.03 |
| 0.041667 | 3.5 | OFF | ON | 94.03 |
| 0.041667 | 3.541667 | OFF | ON | 94.03 |
| 0.041667 | 3.583333 | OFF | ON | 94.03 |
| 0.041667 | 3.625 | OFF | ON | 94.03 |
| 0.041667 | 3.666667 | OFF | ON | 94.03 |
| 0.041667 | 3.708333 | OFF | ON | 94.03 |
| 0.041667 | 3.75 | OFF | ON | 94.03 |
| 0.041667 | 3.791667 | OFF | ON | 94.03 |

-continued

| Each pulse is 0.041677 h | Time in hours | UVC | UVA | % Level of Anthrax Spores on Surface |
|---|---|---|---|---|
| 0.041667 | 3.833333 | OFF | ON | 94.03 |
| 0.041667 | 3.875 | OFF | ON | 94.03 |
| 0.041667 | 3.916667 | OFF | ON | 94.03 |
| 0.041667 | 3.958333 | OFF | ON | 94.03 |
| 0.041667 | 4 | OFF | ON | 94.03 |
| 0.041667 | 4.041667 | OFF | ON | 94.03 |
| 0.041667 | 4.083333 | OFF | ON | 94.03 |
| 0.041667 | 4.125 | OFF | ON | 94.03 |
| 0.041667 | 4.166667 | OFF | ON | 94.03 |
| 0.041667 | 4.208333 | OFF | ON | 94.03 |
| 0.041667 | 4.25 | OFF | ON | 94.03 |
| 0.041667 | 4.291667 | OFF | ON | 94.03 |
| 0.041667 | 4.333333 | OFF | ON | 94.03 |
| 0.041667 | 4.375 | OFF | ON | 94.03 |
| 0.041667 | 4.416667 | OFF | ON | 94.03 |
| 0.041667 | 4.458333 | OFF | ON | 94.03 |
| 0.041667 | 4.5 | OFF | ON | 94.03 |
| 0.041667 | 4.541667 | OFF | ON | 94.03 |
| 0.041667 | 4.583333 | OFF | ON | 94.03 |
| 0.041667 | 4.625 | OFF | ON | 94.03 |
| 0.041667 | 4.666667 | OFF | ON | 94.03 |
| 0.041667 | 4.708333 | OFF | ON | 94.03 |
| 0.041667 | 4.75 | OFF | ON | 94.03 |
| 0.041667 | 4.791667 | OFF | ON | 94.03 |
| 0.041667 | 4.833333 | OFF | ON | 94.03 |
| 0.041667 | 4.875 | OFF | ON | 94.03 |
| 0.041667 | 4.916667 | OFF | ON | 94.03 |
| 0.041667 | 4.958333 | OFF | ON | 94.03 |
| 0.041667 | 5 | OFF | ON | 94.03 |
| 0.041667 | 5.041667 | OFF | ON | 94.03 |
| 0.041667 | 5.083333 | OFF | ON | 94.03 |
| 0.041667 | 5.125 | OFF | ON | 94.03 |
| 0.041667 | 5.166667 | OFF | ON | 94.03 |
| 0.041667 | 5.208333 | OFF | ON | 94.03 |
| 0.041667 | 5.25 | OFF | ON | 94.03 |
| 0.041667 | 5.291667 | OFF | ON | 94.03 |
| 0.041667 | 5.333333 | OFF | ON | 94.03 |
| 0.041667 | 5.375 | OFF | ON | 94.03 |
| 0.041667 | 5.416667 | OFF | ON | 94.03 |
| 0.041667 | 5.458333 | OFF | ON | 94.03 |
| 0.041667 | 5.5 | OFF | ON | 94.03 |
| 0.041667 | 5.541667 | OFF | ON | 94.03 |
| 0.041667 | 5.583333 | OFF | ON | 94.03 |
| 0.041667 | 5.625 | OFF | ON | 94.03 |
| 0.041667 | 5.666667 | OFF | ON | 94.03 |
| 0.041667 | 5.708333 | OFF | ON | 94.03 |
| 0.041667 | 5.75 | OFF | ON | 94.03 |
| 0.041667 | 5.791667 | OFF | ON | 94.03 |
| 0.041667 | 5.833333 | OFF | ON | 94.03 |
| 0.041667 | 5.875 | OFF | ON | 94.03 |
| 0.041667 | 5.916667 | OFF | ON | 94.03 |
| 0.041667 | 5.958333 | OFF | ON | 94.03 |
| 0.041667 | 6 | OFF | ON | 94.03 |
| 0.041667 | 6.041667 | ON | OFF | 88.41641 |
| 0.041667 | 6.083333 | OFF | ON | 88.41641 |
| 0.041667 | 6.125 | OFF | ON | 88.41641 |
| 0.041667 | 6.166667 | OFF | ON | 88.41641 |
| 0.041667 | 6.208333 | OFF | ON | 88.41641 |
| 0.041667 | 6.25 | OFF | ON | 88.41641 |
| 0.041667 | 6.291667 | OFF | ON | 88.41641 |
| 0.041667 | 6.333333 | OFF | ON | 88.41641 |
| 0.041667 | 6.375 | OFF | ON | 88.41641 |
| 0.041667 | 6.416667 | OFF | ON | 88.41641 |
| 0.041667 | 6.458333 | OFF | ON | 88.41641 |
| 0.041667 | 6.5 | OFF | ON | 88.41641 |
| 0.041667 | 6.541667 | OFF | ON | 88.41641 |
| 0.041667 | 6.583333 | OFF | ON | 88.41641 |
| 0.041667 | 6.625 | OFF | ON | 88.41641 |
| 0.041667 | 6.666667 | OFF | ON | 88.41641 |
| 0.041667 | 6.708333 | OFF | ON | 88.41641 |
| 0.041667 | 6.75 | OFF | ON | 88.41641 |
| 0.041667 | 6.791667 | OFF | ON | 88.41641 |
| 0.041667 | 6.833333 | OFF | ON | 88.41641 |
| 0.041667 | 6.875 | OFF | ON | 88.41641 |

-continued

| Each pulse is 0.041677 h | Time in hours | UVC | UVA | % Level of Anthrax Spores on Surface |
|---|---|---|---|---|
| 0.041667 | 6.916667 | OFF | ON | 88.41641 |
| 0.041667 | 6.958333 | OFF | ON | 88.41641 |
| 0.041667 | 7 | OFF | ON | 88.41641 |
| 0.041667 | 7.041667 | OFF | ON | 88.41641 |
| 0.041667 | 7.083333 | OFF | ON | 88.41641 |
| 0.041667 | 7.125 | OFF | ON | 88.41641 |
| 0.041667 | 7.166667 | OFF | ON | 88.41641 |
| 0.041667 | 7.208333 | OFF | ON | 88.41641 |
| 0.041667 | 7.25 | OFF | ON | 88.41641 |
| 0.041667 | 7.291667 | OFF | ON | 88.41641 |
| 0.041667 | 7.333333 | OFF | ON | 88.41641 |
| 0.041667 | 7.375 | OFF | ON | 88.41641 |
| 0.041667 | 7.416667 | OFF | ON | 88.41641 |
| 0.041667 | 7.458333 | OFF | ON | 88.41641 |
| 0.041667 | 7.5 | OFF | ON | 88.41641 |
| 0.041667 | 7.541667 | OFF | ON | 88.41641 |
| 0.041667 | 7.583333 | OFF | ON | 88.41641 |
| 0.041667 | 7.625 | OFF | ON | 88.41641 |
| 0.041667 | 7.666667 | OFF | ON | 88.41641 |
| 0.041667 | 7.708333 | OFF | ON | 88.41641 |
| 0.041667 | 7.75 | OFF | ON | 88.41641 |
| 0.041667 | 7.791667 | OFF | ON | 88.41641 |
| 0.041667 | 7.833333 | OFF | ON | 88.41641 |
| 0.041667 | 7.875 | OFF | ON | 88.41641 |
| 0.041667 | 7.916667 | OFF | ON | 88.41641 |
| 0.041667 | 7.958333 | OFF | ON | 88.41641 |
| 0.041667 | 8 | OFF | ON | 88.41641 |
| 0.041667 | 8.041667 | OFF | ON | 88.41641 |
| 0.041667 | 8.083333 | OFF | ON | 88.41641 |
| 0.041667 | 8.125 | OFF | ON | 88.41641 |
| 0.041667 | 8.166667 | OFF | ON | 88.41641 |
| 0.041667 | 8.208333 | OFF | ON | 88.41641 |
| 0.041667 | 8.25 | OFF | ON | 88.41641 |
| 0.041667 | 8.291667 | OFF | ON | 88.41641 |
| 0.041667 | 8.333333 | OFF | ON | 88.41641 |
| 0.041667 | 8.375 | OFF | ON | 88.41641 |
| 0.041667 | 8.416667 | OFF | ON | 88.41641 |
| 0.041667 | 8.458333 | OFF | ON | 88.41641 |
| 0.041667 | 8.5 | OFF | ON | 88.41641 |
| 0.041667 | 8.541667 | OFF | ON | 88.41641 |
| 0.041667 | 8.583333 | OFF | ON | 88.41641 |
| 0.041667 | 8.625 | OFF | ON | 88.41641 |
| 0.041667 | 8.666667 | OFF | ON | 88.41641 |
| 0.041667 | 8.708333 | OFF | ON | 88.41641 |
| 0.041667 | 8.75 | OFF | ON | 88.41641 |
| 0.041667 | 8.791667 | OFF | ON | 88.41641 |
| 0.041667 | 8.833333 | OFF | ON | 88.41641 |
| 0.041667 | 8.875 | OFF | ON | 88.41641 |
| 0.041667 | 8.916667 | OFF | ON | 88.41641 |
| 0.041667 | 8.958333 | OFF | ON | 88.41641 |
| 0.041667 | 9 | OFF | ON | 88.41641 |
| 0.041667 | 9.041667 | OFF | ON | 88.41641 |
| 0.041667 | 9.083333 | OFF | ON | 88.41641 |
| 0.041667 | 9.125 | OFF | ON | 88.41641 |
| 0.041667 | 9.166667 | OFF | ON | 88.41641 |
| 0.041667 | 9.208333 | OFF | ON | 88.41641 |
| 0.041667 | 9.25 | OFF | ON | 88.41641 |
| 0.041667 | 9.291667 | OFF | ON | 88.41641 |
| 0.041667 | 9.333333 | OFF | ON | 88.41641 |
| 0.041667 | 9.375 | OFF | ON | 88.41641 |
| 0.041667 | 9.416667 | OFF | ON | 88.41641 |
| 0.041667 | 9.458333 | OFF | ON | 88.41641 |
| 0.041667 | 9.5 | OFF | ON | 88.41641 |
| 0.041667 | 9.541667 | OFF | ON | 88.41641 |
| 0.041667 | 9.583333 | OFF | ON | 88.41641 |
| 0.041667 | 9.625 | OFF | ON | 88.41641 |
| 0.041667 | 9.666667 | OFF | ON | 88.41641 |
| 0.041667 | 9.708333 | OFF | ON | 88.41641 |
| 0.041667 | 9.75 | OFF | ON | 88.41641 |
| 0.041667 | 9.791667 | OFF | ON | 88.41641 |
| 0.041667 | 9.833333 | OFF | ON | 88.41641 |
| 0.041667 | 9.875 | OFF | ON | 88.41641 |
| 0.041667 | 9.916667 | OFF | ON | 88.41641 |
| 0.041667 | 9.958333 | OFF | ON | 88.41641 |

| Each pulse is 0.041677 h | Time in hours | UVC | UVA | % Level of Anthrax Spores on Surface |
|---|---|---|---|---|
| 0.041667 | 10 | OFF | ON | 88.41641 |
| 0.041667 | 10.04167 | OFF | ON | 88.41641 |
| 0.041667 | 10.08333 | OFF | ON | 88.41641 |
| 0.041667 | 10.125 | OFF | ON | 88.41641 |
| 0.041667 | 10.16667 | OFF | ON | 88.41641 |
| 0.041667 | 10.20833 | OFF | ON | 88.41641 |
| 0.041667 | 10.25 | OFF | ON | 88.41641 |
| 0.041667 | 10.29167 | OFF | ON | 88.41641 |
| 0.041667 | 10.33333 | OFF | ON | 88.41641 |
| 0.041667 | 10.375 | OFF | ON | 88.41641 |
| 0.041667 | 10.41667 | OFF | ON | 88.41641 |
| 0.041667 | 10.45833 | OFF | ON | 88.41641 |
| 0.041667 | 10.5 | OFF | ON | 88.41641 |
| 0.041667 | 10.54167 | OFF | ON | 88.41641 |
| 0.041667 | 10.58333 | OFF | ON | 88.41641 |
| 0.041667 | 10.625 | OFF | ON | 88.41641 |
| 0.041667 | 10.66667 | OFF | ON | 88.41641 |
| 0.041667 | 10.70833 | OFF | ON | 88.41641 |
| 0.041667 | 10.75 | OFF | ON | 88.41641 |
| 0.041667 | 10.79167 | OFF | ON | 88.41641 |
| 0.041667 | 10.83333 | OFF | ON | 88.41641 |
| 0.041667 | 10.875 | OFF | ON | 88.41641 |
| 0.041667 | 10.91667 | OFF | ON | 88.41641 |
| 0.041667 | 10.95833 | OFF | ON | 88.41641 |
| 0.041667 | 11 | OFF | ON | 88.41641 |
| 0.041667 | 11.04167 | OFF | ON | 88.41641 |
| 0.041667 | 11.08333 | OFF | ON | 88.41641 |
| 0.041667 | 11.125 | OFF | ON | 88.41641 |
| 0.041667 | 11.16667 | OFF | ON | 88.41641 |
| 0.041667 | 11.20833 | OFF | ON | 88.41641 |
| 0.041667 | 11.25 | OFF | ON | 88.41641 |
| 0.041667 | 11.29167 | OFF | ON | 88.41641 |
| 0.041667 | 11.33333 | OFF | ON | 88.41641 |
| 0.041667 | 11.375 | OFF | ON | 88.41641 |
| 0.041667 | 11.41667 | OFF | ON | 88.41641 |
| 0.041667 | 11.45833 | OFF | ON | 88.41641 |
| 0.041667 | 11.5 | OFF | ON | 88.41641 |
| 0.041667 | 11.54167 | OFF | ON | 88.41641 |
| 0.041667 | 11.58333 | OFF | ON | 88.41641 |
| 0.041667 | 11.625 | OFF | ON | 88.41641 |
| 0.041667 | 11.66667 | OFF | ON | 88.41641 |
| 0.041667 | 11.70833 | OFF | ON | 88.41641 |
| 0.041667 | 11.75 | OFF | ON | 88.41641 |
| 0.041667 | 11.79167 | OFF | ON | 88.41641 |
| 0.041667 | 11.83333 | OFF | ON | 88.41641 |
| 0.041667 | 11.875 | OFF | ON | 88.41641 |
| 0.041667 | 11.91667 | OFF | ON | 88.41641 |
| 0.041667 | 11.95833 | OFF | ON | 88.41641 |
| 0.041667 | 12 | OFF | ON | 88.41641 |
| 0.041667 | 12.04167 | ON | OFF | 83.13795 |
| 0.041667 | 12.08333 | OFF | ON | 83.13795 |
| 0.041667 | 12.125 | OFF | ON | 83.13795 |
| 0.041667 | 12.16667 | OFF | ON | 83.13795 |
| 0.041667 | 12.20833 | OFF | ON | 83.13795 |
| 0.041667 | 12.25 | OFF | ON | 83.13795 |
| 0.041667 | 12.29167 | OFF | ON | 83.13795 |
| 0.041667 | 12.33333 | OFF | ON | 83.13795 |
| 0.041667 | 12.375 | OFF | ON | 83.13795 |
| 0.041667 | 12.41667 | OFF | ON | 83.13795 |
| 0.041667 | 12.45833 | OFF | ON | 83.13795 |
| 0.041667 | 12.5 | OFF | ON | 83.13795 |
| 0.041667 | 12.54167 | OFF | ON | 83.13795 |
| 0.041667 | 12.58333 | OFF | ON | 83.13795 |
| 0.041667 | 12.625 | OFF | ON | 83.13795 |
| 0.041667 | 12.66667 | OFF | ON | 83.13795 |
| 0.041667 | 12.70833 | OFF | ON | 83.13795 |
| 0.041667 | 12.75 | OFF | ON | 83.13795 |
| 0.041667 | 12.79167 | OFF | ON | 83.13795 |
| 0.041667 | 12.83333 | OFF | ON | 83.13795 |
| 0.041667 | 12.875 | OFF | ON | 83.13795 |
| 0.041667 | 12.91667 | OFF | ON | 83.13795 |
| 0.041667 | 12.95833 | OFF | ON | 83.13795 |
| 0.041667 | 13 | OFF | ON | 83.13795 |
| 0.041667 | 13.04167 | OFF | ON | 83.13795 |
| 0.041667 | 13.08333 | OFF | ON | 83.13795 |
| 0.041667 | 13.125 | OFF | ON | 83.13795 |
| 0.041667 | 13.16667 | OFF | ON | 83.13795 |
| 0.041667 | 13.20833 | OFF | ON | 83.13795 |
| 0.041667 | 13.25 | OFF | ON | 83.13795 |
| 0.041667 | 13.29167 | OFF | ON | 83.13795 |
| 0.041667 | 13.33333 | OFF | ON | 83.13795 |
| 0.041667 | 13.375 | OFF | ON | 83.13795 |
| 0.041667 | 13.41667 | OFF | ON | 83.13795 |
| 0.041667 | 13.45833 | OFF | ON | 83.13795 |
| 0.041667 | 13.5 | OFF | ON | 83.13795 |
| 0.041667 | 13.54167 | OFF | ON | 83.13795 |
| 0.041667 | 13.58333 | OFF | ON | 83.13795 |
| 0.041667 | 13.625 | OFF | ON | 83.13795 |
| 0.041667 | 13.66667 | OFF | ON | 83.13795 |
| 0.041667 | 13.70833 | OFF | ON | 83.13795 |
| 0.041667 | 13.75 | OFF | ON | 83.13795 |
| 0.041667 | 13.79167 | OFF | ON | 83.13795 |
| 0.041667 | 13.83333 | OFF | ON | 83.13795 |
| 0.041667 | 13.875 | OFF | ON | 83.13795 |
| 0.041667 | 13.91667 | OFF | ON | 83.13795 |
| 0.041667 | 13.95833 | OFF | ON | 83.13795 |
| 0.041667 | 14 | OFF | ON | 83.13795 |
| 0.041667 | 14.04167 | OFF | ON | 83.13795 |
| 0.041667 | 14.08333 | OFF | ON | 83.13795 |
| 0.041667 | 14.125 | OFF | ON | 83.13795 |
| 0.041667 | 14.16667 | OFF | ON | 83.13795 |
| 0.041667 | 14.20833 | OFF | ON | 83.13795 |
| 0.041667 | 14.25 | OFF | ON | 83.13795 |
| 0.041667 | 14.29167 | OFF | ON | 83.13795 |
| 0.041667 | 14.33333 | OFF | ON | 83.13795 |
| 0.041667 | 14.375 | OFF | ON | 83.13795 |
| 0.041667 | 14.41667 | OFF | ON | 83.13795 |
| 0.041667 | 14.45833 | OFF | ON | 83.13795 |
| 0.041667 | 14.5 | OFF | ON | 83.13795 |
| 0.041667 | 14.54167 | OFF | ON | 83.13795 |
| 0.041667 | 14.58333 | OFF | ON | 83.13795 |
| 0.041667 | 14.625 | OFF | ON | 83.13795 |
| 0.041667 | 14.66667 | OFF | ON | 83.13795 |
| 0.041667 | 14.70833 | OFF | ON | 83.13795 |
| 0.041667 | 14.75 | OFF | ON | 83.13795 |
| 0.041667 | 14.79167 | OFF | ON | 83.13795 |
| 0.041667 | 14.83333 | OFF | ON | 83.13795 |
| 0.041667 | 14.875 | OFF | ON | 83.13795 |
| 0.041667 | 14.91667 | OFF | ON | 83.13795 |
| 0.041667 | 14.95833 | OFF | ON | 83.13795 |
| 0.041667 | 15 | OFF | ON | 83.13795 |
| 0.041667 | 15.04167 | OFF | ON | 83.13795 |
| 0.041667 | 15.08333 | OFF | ON | 83.13795 |
| 0.041667 | 15.125 | OFF | ON | 83.13795 |
| 0.041667 | 15.16667 | OFF | ON | 83.13795 |
| 0.041667 | 15.20833 | OFF | ON | 83.13795 |
| 0.041667 | 15.25 | OFF | ON | 83.13795 |
| 0.041667 | 15.29167 | OFF | ON | 83.13795 |
| 0.041667 | 15.33333 | OFF | ON | 83.13795 |
| 0.041667 | 15.375 | OFF | ON | 83.13795 |
| 0.041667 | 15.41667 | OFF | ON | 83.13795 |
| 0.041667 | 15.45833 | OFF | ON | 83.13795 |
| 0.041667 | 15.5 | OFF | ON | 83.13795 |
| 0.041667 | 15.54167 | OFF | ON | 83.13795 |
| 0.041667 | 15.58333 | OFF | ON | 83.13795 |
| 0.041667 | 15.625 | OFF | ON | 83.13795 |
| 0.041667 | 15.66667 | OFF | ON | 83.13795 |
| 0.041667 | 15.70833 | OFF | ON | 83.13795 |
| 0.041667 | 15.75 | OFF | ON | 83.13795 |
| 0.041667 | 15.79167 | OFF | ON | 83.13795 |
| 0.041667 | 15.83333 | OFF | ON | 83.13795 |
| 0.041667 | 15.875 | OFF | ON | 83.13795 |
| 0.041667 | 15.91667 | OFF | ON | 83.13795 |
| 0.041667 | 15.95833 | OFF | ON | 83.13795 |
| 0.041667 | 16 | OFF | ON | 83.13795 |
| 0.041667 | 16.04167 | OFF | ON | 83.13795 |
| 0.041667 | 16.08333 | OFF | ON | 83.13795 |
| 0.041667 | 16.125 | OFF | ON | 83.13795 |

-continued

| Each pulse is 0.041677 h | Time in hours | UVC | UVA | % Level of Anthrax Spores on Surface |
|---|---|---|---|---|
| 0.041667 | 16.16667 | OFF | ON | 83.13795 |
| 0.041667 | 16.20833 | OFF | ON | 83.13795 |
| 0.041667 | 16.25 | OFF | ON | 83.13795 |
| 0.041667 | 16.29167 | OFF | ON | 83.13795 |
| 0.041667 | 16.33333 | OFF | ON | 83.13795 |
| 0.041667 | 16.375 | OFF | ON | 83.13795 |
| 0.041667 | 16.41667 | OFF | ON | 83.13795 |
| 0.041667 | 16.45833 | OFF | ON | 83.13795 |
| 0.041667 | 16.5 | OFF | ON | 83.13795 |
| 0.041667 | 16.54167 | OFF | ON | 83.13795 |
| 0.041667 | 16.58333 | OFF | ON | 83.13795 |
| 0.041667 | 16.625 | OFF | ON | 83.13795 |
| 0.041667 | 16.66667 | OFF | ON | 83.13795 |
| 0.041667 | 16.70833 | OFF | ON | 83.13795 |
| 0.041667 | 16.75 | OFF | ON | 83.13795 |
| 0.041667 | 16.79167 | OFF | ON | 83.13795 |
| 0.041667 | 16.83333 | OFF | ON | 83.13795 |
| 0.041667 | 16.875 | OFF | ON | 83.13795 |
| 0.041667 | 16.91667 | OFF | ON | 83.13795 |
| 0.041667 | 16.95833 | OFF | ON | 83.13795 |
| 0.041667 | 17 | OFF | ON | 83.13795 |
| 0.041667 | 17.04167 | OFF | ON | 83.13795 |
| 0.041667 | 17.08333 | OFF | ON | 83.13795 |
| 0.041667 | 17.125 | OFF | ON | 83.13795 |
| 0.041667 | 17.16667 | OFF | ON | 83.13795 |
| 0.041667 | 17.20833 | OFF | ON | 83.13795 |
| 0.041667 | 17.25 | OFF | ON | 83.13795 |
| 0.041667 | 17.29167 | OFF | ON | 83.13795 |
| 0.041667 | 17.33333 | OFF | ON | 83.13795 |
| 0.041667 | 17.375 | OFF | ON | 83.13795 |
| 0.041667 | 17.41667 | OFF | ON | 83.13795 |
| 0.041667 | 17.45833 | OFF | ON | 83.13795 |
| 0.041667 | 17.5 | OFF | ON | 83.13795 |
| 0.041667 | 17.54167 | OFF | ON | 83.13795 |
| 0.041667 | 17.58333 | OFF | ON | 83.13795 |
| 0.041667 | 17.625 | OFF | ON | 83.13795 |
| 0.041667 | 17.66667 | OFF | ON | 83.13795 |
| 0.041667 | 17.70833 | OFF | ON | 83.13795 |
| 0.041667 | 17.75 | OFF | ON | 83.13795 |
| 0.041667 | 17.79167 | OFF | ON | 83.13795 |
| 0.041667 | 17.83333 | OFF | ON | 83.13795 |
| 0.041667 | 17.875 | OFF | ON | 83.13795 |
| 0.041667 | 17.91667 | OFF | ON | 83.13795 |
| 0.041667 | 17.95833 | OFF | ON | 83.13795 |
| 0.041667 | 18 | OFF | ON | 83.13795 |
| 0.041667 | 18.04167 | ON | OFF | 78.17461 |
| 0.041667 | 18.08333 | OFF | ON | 78.17461 |
| 0.041667 | 18.125 | OFF | ON | 78.17461 |
| 0.041667 | 18.16667 | OFF | ON | 78.17461 |
| 0.041667 | 18.20833 | OFF | ON | 78.17461 |
| 0.041667 | 18.25 | OFF | ON | 78.17461 |
| 0.041667 | 18.29167 | OFF | ON | 78.17461 |
| 0.041667 | 18.33333 | OFF | ON | 78.17461 |
| 0.041667 | 18.375 | OFF | ON | 78.17461 |
| 0.041667 | 18.41667 | OFF | ON | 78.17461 |
| 0.041667 | 18.45833 | OFF | ON | 78.17461 |
| 0.041667 | 18.5 | OFF | ON | 78.17461 |
| 0.041667 | 18.54167 | OFF | ON | 78.17461 |
| 0.041667 | 18.58333 | OFF | ON | 78.17461 |
| 0.041667 | 18.625 | OFF | ON | 78.17461 |
| 0.041667 | 18.66667 | OFF | ON | 78.17461 |
| 0.041667 | 18.70833 | OFF | ON | 78.17461 |
| 0.041667 | 18.75 | OFF | ON | 78.17461 |
| 0.041667 | 18.79167 | OFF | ON | 78.17461 |
| 0.041667 | 18.83333 | OFF | ON | 78.17461 |
| 0.041667 | 18.875 | OFF | ON | 78.17461 |
| 0.041667 | 18.91667 | OFF | ON | 78.17461 |
| 0.041667 | 18.95833 | OFF | ON | 78.17461 |
| 0.041667 | 19 | OFF | ON | 78.17461 |
| 0.041667 | 19.04167 | OFF | ON | 78.17461 |
| 0.041667 | 19.08333 | OFF | ON | 78.17461 |
| 0.041667 | 19.125 | OFF | ON | 78.17461 |
| 0.041667 | 19.16667 | OFF | ON | 78.17461 |
| 0.041667 | 19.20833 | OFF | ON | 78.17461 |
| 0.041667 | 19.25 | OFF | ON | 78.17461 |
| 0.041667 | 19.29167 | OFF | ON | 78.17461 |
| 0.041667 | 19.33333 | OFF | ON | 78.17461 |
| 0.041667 | 19.375 | OFF | ON | 78.17461 |
| 0.041667 | 19.41667 | OFF | ON | 78.17461 |
| 0.041667 | 19.45833 | OFF | ON | 78.17461 |
| 0.041667 | 19.5 | OFF | ON | 78.17461 |
| 0.041667 | 19.54167 | OFF | ON | 78.17461 |
| 0.041667 | 19.58333 | OFF | ON | 78.17461 |
| 0.041667 | 19.625 | OFF | ON | 78.17461 |
| 0.041667 | 19.66667 | OFF | ON | 78.17461 |
| 0.041667 | 19.70833 | OFF | ON | 78.17461 |
| 0.041667 | 19.75 | OFF | ON | 78.17461 |
| 0.041667 | 19.79167 | OFF | ON | 78.17461 |
| 0.041667 | 19.83333 | OFF | ON | 78.17461 |
| 0.041667 | 19.875 | OFF | ON | 78.17461 |
| 0.041667 | 19.91667 | OFF | ON | 78.17461 |
| 0.041667 | 19.95833 | OFF | ON | 78.17461 |
| 0.041667 | 20 | OFF | ON | 78.17461 |
| 0.041667 | 20.04167 | OFF | ON | 78.17461 |
| 0.041667 | 20.08333 | OFF | ON | 78.17461 |
| 0.041667 | 20.125 | OFF | ON | 78.17461 |
| 0.041667 | 20.16667 | OFF | ON | 78.17461 |
| 0.041667 | 20.20833 | OFF | ON | 78.17461 |
| 0.041667 | 20.25 | OFF | ON | 78.17461 |
| 0.041667 | 20.29167 | OFF | ON | 78.17461 |
| 0.041667 | 20.33333 | OFF | ON | 78.17461 |
| 0.041667 | 20.375 | OFF | ON | 78.17461 |
| 0.041667 | 20.41667 | OFF | ON | 78.17461 |
| 0.041667 | 20.45833 | OFF | ON | 78.17461 |
| 0.041667 | 20.5 | OFF | ON | 78.17461 |
| 0.041667 | 20.54167 | OFF | ON | 78.17461 |
| 0.041667 | 20.58333 | OFF | ON | 78.17461 |
| 0.041667 | 20.625 | OFF | ON | 78.17461 |
| 0.041667 | 20.66667 | OFF | ON | 78.17461 |
| 0.041667 | 20.70833 | OFF | ON | 78.17461 |
| 0.041667 | 20.75 | OFF | ON | 78.17461 |
| 0.041667 | 20.79167 | OFF | ON | 78.17461 |
| 0.041667 | 20.83333 | OFF | ON | 78.17461 |
| 0.041667 | 20.875 | OFF | ON | 78.17461 |
| 0.041667 | 20.91667 | OFF | ON | 78.17461 |
| 0.041667 | 20.95833 | OFF | ON | 78.17461 |
| 0.041667 | 21 | OFF | ON | 78.17461 |
| 0.041667 | 21.04167 | OFF | ON | 78.17461 |
| 0.041667 | 21.08333 | OFF | ON | 78.17461 |
| 0.041667 | 21.125 | OFF | ON | 78.17461 |
| 0.041667 | 21.16667 | OFF | ON | 78.17461 |
| 0.041667 | 21.20833 | OFF | ON | 78.17461 |
| 0.041667 | 21.25 | OFF | ON | 78.17461 |
| 0.041667 | 21.29167 | OFF | ON | 78.17461 |
| 0.041667 | 21.33333 | OFF | ON | 78.17461 |
| 0.041667 | 21.375 | OFF | ON | 78.17461 |
| 0.041667 | 21.41667 | OFF | ON | 78.17461 |
| 0.041667 | 21.45833 | OFF | ON | 78.17461 |
| 0.041667 | 21.5 | OFF | ON | 78.17461 |
| 0.041667 | 21.54167 | OFF | ON | 78.17461 |
| 0.041667 | 21.58333 | OFF | ON | 78.17461 |
| 0.041667 | 21.625 | OFF | ON | 78.17461 |
| 0.041667 | 21.66667 | OFF | ON | 78.17461 |
| 0.041667 | 21.70833 | OFF | ON | 78.17461 |
| 0.041667 | 21.75 | OFF | ON | 78.17461 |
| 0.041667 | 21.79167 | OFF | ON | 78.17461 |
| 0.041667 | 21.83333 | OFF | ON | 78.17461 |
| 0.041667 | 21.875 | OFF | ON | 78.17461 |
| 0.041667 | 21.91667 | OFF | ON | 78.17461 |
| 0.041667 | 21.95833 | OFF | ON | 78.17461 |
| 0.041667 | 22 | OFF | ON | 78.17461 |
| 0.041667 | 22.04167 | OFF | ON | 78.17461 |
| 0.041667 | 22.08333 | OFF | ON | 78.17461 |
| 0.041667 | 22.125 | OFF | ON | 78.17461 |
| 0.041667 | 22.16667 | OFF | ON | 78.17461 |
| 0.041667 | 22.20833 | OFF | ON | 78.17461 |
| 0.041667 | 22.25 | OFF | ON | 78.17461 |
| 0.041667 | 22.29167 | OFF | ON | 78.17461 |

-continued

| Each pulse is 0.041677 h | Time in hours | UVC | UVA | % Level of Anthrax Spores on Surface |
|---|---|---|---|---|
| 0.041667 | 22.33333 | OFF | ON | 78.17461 |
| 0.041667 | 22.375 | OFF | ON | 78.17461 |
| 0.041667 | 22.41667 | OFF | ON | 78.17461 |
| 0.041667 | 22.45833 | OFF | ON | 78.17461 |
| 0.041667 | 22.5 | OFF | ON | 78.17461 |
| 0.041667 | 22.54167 | OFF | ON | 78.17461 |
| 0.041667 | 22.58333 | OFF | ON | 78.17461 |
| 0.041667 | 22.625 | OFF | ON | 78.17461 |
| 0.041667 | 22.66667 | OFF | ON | 78.17461 |
| 0.041667 | 22.70833 | OFF | ON | 78.17461 |
| 0.041667 | 22.75 | OFF | ON | 78.17461 |
| 0.041667 | 22.79167 | OFF | ON | 78.17461 |
| 0.041667 | 22.83333 | OFF | ON | 78.17461 |
| 0.041667 | 22.875 | OFF | ON | 78.17461 |
| 0.041667 | 22.91667 | OFF | ON | 78.17461 |
| 0.041667 | 22.95833 | OFF | ON | 78.17461 |
| 0.041667 | 23 | OFF | ON | 78.17461 |
| 0.041667 | 23.04167 | OFF | ON | 78.17461 |
| 0.041667 | 23.08333 | OFF | ON | 78.17461 |
| 0.041667 | 23.125 | OFF | ON | 78.17461 |
| 0.041667 | 23.16667 | OFF | ON | 78.17461 |
| 0.041667 | 23.20833 | OFF | ON | 78.17461 |
| 0.041667 | 23.25 | OFF | ON | 78.17461 |
| 0.041667 | 23.29167 | OFF | ON | 78.17461 |
| 0.041667 | 23.33333 | OFF | ON | 78.17461 |
| 0.041667 | 23.375 | OFF | ON | 78.17461 |
| 0.041667 | 23.41667 | OFF | ON | 78.17461 |
| 0.041667 | 23.45833 | OFF | ON | 78.17461 |
| 0.041667 | 23.5 | OFF | ON | 78.17461 |
| 0.041667 | 23.54167 | OFF | ON | 78.17461 |
| 0.041667 | 23.58333 | OFF | ON | 78.17461 |
| 0.041667 | 23.625 | OFF | ON | 78.17461 |
| 0.041667 | 23.66667 | OFF | ON | 78.17461 |
| 0.041667 | 23.70833 | OFF | ON | 78.17461 |
| 0.041667 | 23.75 | OFF | ON | 78.17461 |
| 0.041667 | 23.79167 | OFF | ON | 78.17461 |
| 0.041667 | 23.83333 | OFF | ON | 78.17461 |
| 0.041667 | 23.875 | OFF | ON | 78.17461 |
| 0.041667 | 23.91667 | OFF | ON | 78.17461 |
| 0.041667 | 23.95833 | OFF | ON | 78.17461 |
| 0.041667 | 24 | OFF | ON | 78.17461 |

As may be seen from the above, when the UVC is pulsed on, the bacteria is killed to a certain level and UVC is pulsed off with UVA pulsed on keeping the bacteria level the same without any growth. The UVA is then pulsed off and UVC is pulsed on with further bacteria kill and subsequent UVA on after UVC is off maintains the new lower level of bacteria on the surface (i.e. further growth inhibition. The ON/OFF pulsing method reduces the level of bacteria on the surface by about 20% between 12-18 hours and inhibits bacteria growth for at least 24 hours while keeping radiation levels safe for humans.

Example 5

UVA/UVC Pulsing Compared to No UV on E. Coli K12

Abbreviations

ATP: Adenosine triphosphate, CFU: Colony forming unit, RLU: Relative luminescence units, SEM; Standard error of the mean, TNTC: Too numerous to count, UVA: Ultraviolet A, UVC: Ultraviolet C.

Materials

Nutrient agar, maximum recovery diluent, violet red bile glucose agar and tryptone soya broth was purchased from Oxoid Ltd (Basingstoke, Hampshire UK). Petri dishes were purchased from Scientific Lab Supplies Ltd UK. Ultra-Snap™ Adenosine triphosphate (ATP) surface tests were purchased from Hygiena International Ltd. E. Coli K12 was purchased from Blades Biological Ltd (East Sussex, UK).

Equipment

Figure 3:
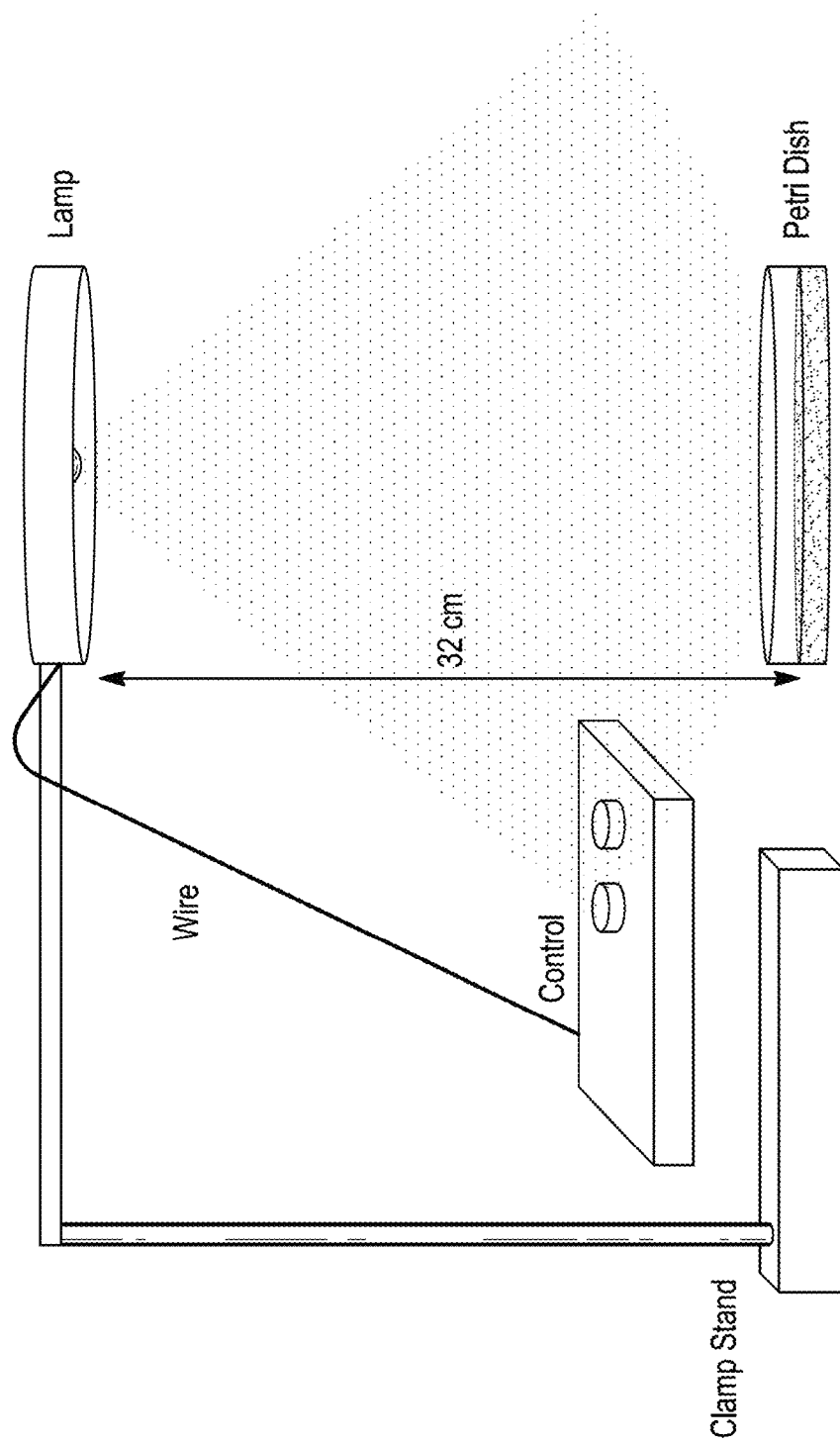
FIG. 3 is the equipment set up for Example 5.

Referring now to FIG. 3, scheme of equipment set up (not to scale). The two buttons on the control box represent the UVA and UVC switches. The lamp was placed 32 cm away from the petri dish.

The equipment was housed in a Syngene Bioimaging light box for protection of exposure to UVA and UVC. The wire from the lamp was wrapped around the clamp stand in order to ensure that the lamp was fully exposing the petri dish. The lamp was placed 32 cm away from the petri dish. The lamp and control box were provided by Helios. The autoclave was an Eclipse 17 and a Genlab incubator was used for organism growth. The temperature of the box was maintained at room temperature. A Hygiena luminometer was used for ATP readings.

EXPERIMENTAL

Micro-Organism and Culture Methods

Test organism was E. Coli K12. Agar was sterilised at 121° C. The organism was grown in tryptone soya broth and incubated for 12 hours at 37° C. E. Coli K12 was validated using violet red bile glucose agar. Maximal recovery diluent was autoclaved prior to use. E. Coli K12 was diluted to 1 in 10,000 in maximal recovery diluent in order to be counted using a lawn plate approach. 10 µL of E. Coli K12 was pipetted in four different areas on the nutrient three agar plate in sterile conditions. The plates were then stored in one of three conditions: dark, natural light and UV light. The details regarding the UV light exposure are recorded in Protocol I and Protocol II. After exposure, plates were incubated for 24 hours at 37° C. and colonies were counted.

Protocol I

Non-Treated plates were exposed to natural light and dark conditions.

Protocol II

UVA, nominal wavelength of 405 nm, was set to a power intensity of 42 mW, and UVC nominal wavelength of 275 nm, was set to a power intensity of 117 mW. UVC was engaged with UVA extinguished for 3 minutes and UVA engaged for 30 minutes with UVC extinguished. This was completed for a total of $10^{-13}$ cycles with a total exposure time between 330 minutes and 429 minutes, respectively.

ATP Measurement

ATP measurements were conducted in instances where no visible colonies were present. The UltraSnap™ swabs were equilibrated at room temperature. The surface of the petri dish was swabbed thoroughly. The swab was replaced back into the tube and the tube was placed into the Hygiena luminometer within 30 seconds and ATP levels were recorded. Readings less than 10 relative luminescence units (RLU) are considered clean. Readings between 11-29 RLU indicate a warning and readings above 30 RLU indicate a dirty surface.

CFU Assessment

Colony forming units (CFUs) are counted based on the number of viable bacterial cells. This is undertaken with the aid of a microscope. The number of bacteria per mL of sample is calculated by dividing the colony number by the dilution factor employed. This is a direct count method.

Results

The survival of the E. Coli K12 was monitored over different time periods.

Protocol I

The bacterial growth present were too numerous to count (TNTC) on the dark and natural light plates hence it was not possible to determine the number of colony forming units (CFU). In order to assess the surface, ATP measurements were performed.

| Time | ATP (RLU) Dark | Natural Light |
|---|---|---|
| 12 hours | 5389 | 7496 |

Table 1: Measurements of ATP in RLU in Dark and Natural Light Conditions

The differences in levels of dark and natural light bacteria are due to within day variations as there will be a small difference in temperature and amount of light exposed.

Protocol II

Following 3 repetitions of 13 iterations of Protocol II described above, we observed a 32±3% (average±standard error of the mean (SEM)) reduction in CFU on comparison of the UV exposed bacteria in comparison to the bacteria stored in natural light. These values may change considering different distances and different intensity and time periods for pulsing.

| Repeat | Average/ 10 ul | Standard Deviation | Average CFU/1 ml | % Difference |
|---|---|---|---|---|
| 1 | 11.5 | 1.12 | 1150 | 28.26 |
| 2 | 8.5 | 2.22 | 850 | 33.33 |
| 3 | 4.9 | 1.88 | 486 | 35.29 |

| Average % Difference | SD % Difference | SEM % Difference |
|---|---|---|
| 32.296 | 2.964 | 2.095 |

Table 2. Summary of Effects from UV Protocol II on Bacterial Load for 13 Cycles

Following 10 cycles of the protocol described above we observed a 6% reduction in bacterial load, on comparison of the bacteria exposed to UV light compared to the dark. This shows that differences are observed with less exposure time to the UV light using this pulse sequence.

| Condition Comparison | Average % Difference | SD % Difference | SEM % Difference |
|---|---|---|---|
| UV/Dark | 35.0 | 12.3 | 8.7 |
| UV/Natural Light | 32.3 | 3.0 | 2.1 |

Table 3. Comparisons of Conditions (Natural Light Vs Dark) on Data from 13 Cycles.

A 32±3% reduction in bacterial load across a 13 iteration repeat of 33 minute irradiation cycles (Protocol II) is shown. Additionally, Protocol II compared to controls exposed to natural light and dark elicited a 35±12% reduction in bacterial load.

Example 6

UVA/UVC Pulsing on *E. Coli* K12, *Bacillus Subtilis* and *Staphylococcus Epidermidis*

This example investigated UVA and UVC irradiation on an array of bacteria considering a variety of power settings and times, the impact of UVA and UVC pulsing on an array of bacteria considering a variety of distances and exposure times and to use modelling in order to establish cross contamination risk following exposure with UV light.

Materials

Nutrient agar, maximum recovery diluent, violet red bile glucose agar and tryptone soya broth was purchased from Oxoid Ltd (Basingstoke, Hampshire UK). Single vent petri dishes were purchased from Scientific Lab Supplies Ltd UK. UltraSnap™ Adenosine triphosphate (ATP) surface tests were purchased from Hygiena International Ltd. *Escherichia Coli* K12. *Bacillus Subtilis* and *Staphylococcus Epidermidis* was purchased from Blades Biological Ltd (East Sussex, UK).

Equipment

Figure 4:
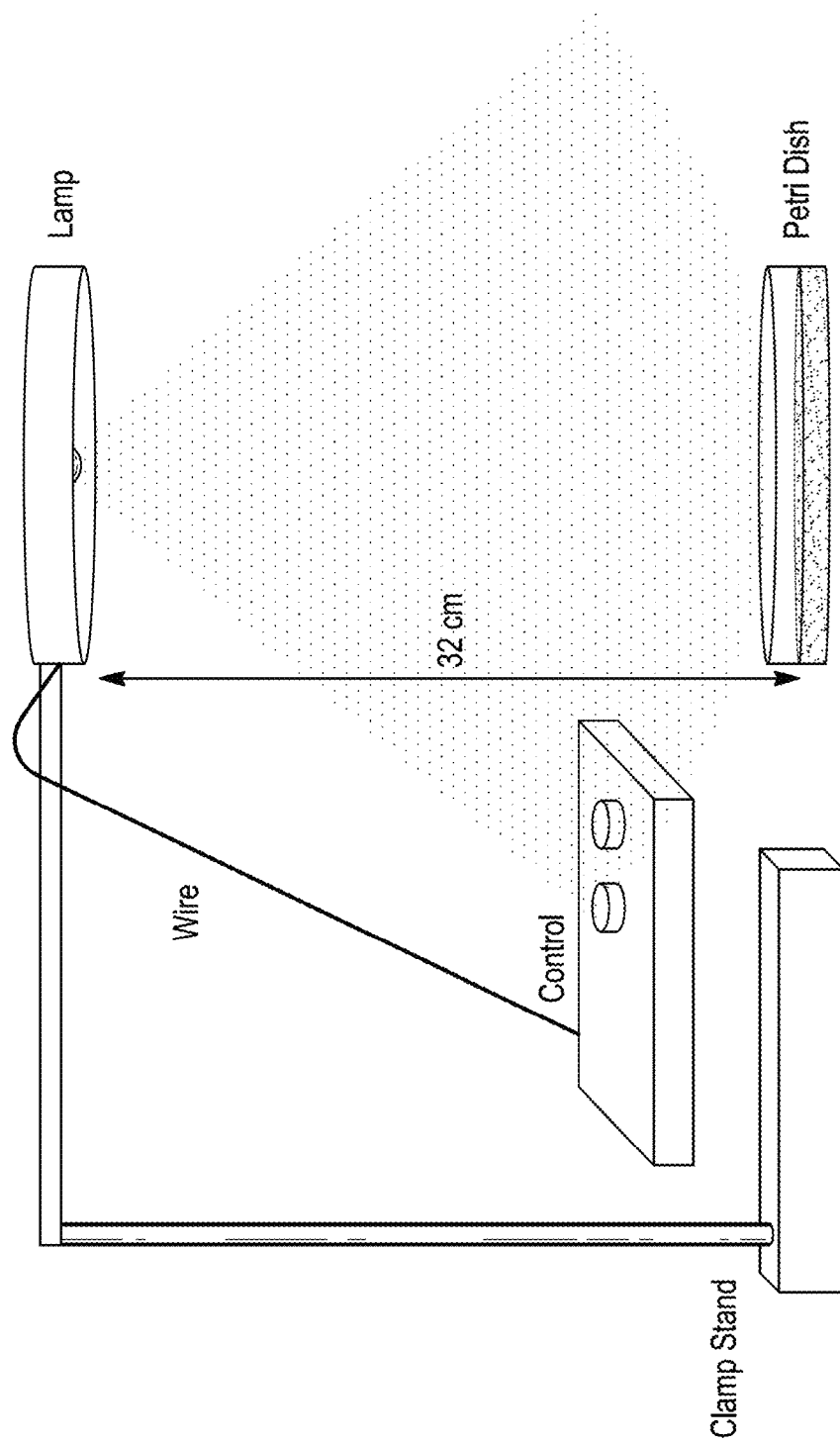
FIG. 4 is the equipment set up for Example 6.

Referring now to FIG. 4, scheme of equipment set up (not to scale). Blue (outerlined) box represents the housing of the equipment in light box. The two green buttons on the control represent the UVA and UVC switches. The lamp was placed 32 cm away from the petri dish.

The equipment was housed in a Syngene Bioimaging light box for protection of exposure to UVA and UVC. The wire from the lamp was wrapped around the clamp stand in order to ensure that the petri dish was fully exposed to the lamp. The lamp was placed 32 cm away from the petri dish for all experiments with exception to where different distances are stated. The lamp and control were provided by Helios Shield Ltd. UVA and UVC exposure dials were utilised for direct exposure. The control stated a total of 16 different settings for the lamp. This apparatus assembly was constructed in Nottingham Trent University, UK.

The autoclave (Eclipse 17) was utilised in order to sterilise all equipment and a Genlab incubator was used for organism growth which was maintained at 37° C. throughout the experiment period. The temperature of the box was maintained at room temperature which fluctuated between 18° C. and 25° C. A Hygiena luminometer was used for ATP readings.

This experimental design set up is similar to that described by Bolton, J. R. and Linden, K. G. (2003) Standardization of Methods for Fluence (UV Dosage) Determination in Bench-Scale UV Experiments. *Journal of Environmental Engineering* 129 (3) 209-215).

This research article outlined the importance of standardising UV experiment bench-scale experimental set up, and was one of highlighted discussion points. The only missing attribute from the experimental set up described herein is the use of a stirrer and petri dish (Bolton and Linden 2003) however, this is deemed inappropriate for the methodology due to using a lawn plate approach.

Experimental

Micro-Organism and Culture Methods

Test organisms include *E. Coli* K12, *B. Subtilis* and *S. Epidermidis*. Nutrient agar and violet blue red agar were prepared, as per the protocol from the manufacturer, and was sterilised at 121° C. and 110.4 kPa for a 1 hour period. Both types of agar were poured into singlet vent petri dishes, left to dry and set before being stored at 4° C. prior to use. Organisms (*B. Subtilis* and *S. Epidermidis*) were grown in tryptone soya broth and incubated for 12 hours at 37° C. *E. Coli* K12 was validated using violet red bile glucose agar using the streaking method. *B. Subtilis* and *S. Epidermidis* were validated using the Nutrient agar. Maximal recovery diluent was autoclaved prior to use. *E. Coli* K12. *B. Subtilis* and *S. Epidermidis* was diluted to 1 in 10,000 in maximal recovery diluent in order to be counted using a lawn plate approach. 10 μL of *E. Coli* K12 was pipetted in different areas on the nutrient three nutrient agar plates under sterile conditions. The plates were then stored in one of three conditions: dark, natural light and UV light for different periods of time. The details regarding the UV light exposure, time of exposure and distance from the UV lamp are recorded in Protocol I and Protocol II below. After exposure, plates were incubated for 24 hours at 37° C. and colonies were counted. In the instances where the bacteria was too numerous to count (TNTC), ATP measurements were performed.

Protocol I

UVA and UVC were used simultaneously on the agar plates for a period of 12 hours using various power levels including 42 mW, 117 mW and 65 mW. This was performed for all microorganisms in the investigation, E. Coli K12. B. Subtilis and S. Epidermidis. The bacteria were then grown for a 24 hour period and data was acquired.

Protocol II

UVA and UVC were pulsed using power levels 42 mW and 65 mW, respectively. UVC was engaged for 3 minutes, then UVC was disengaged. Subsequently UVA was engaged for 30 minutes and then UVA was disengaged. This was completed for a total of $10^{-13}$ iterations with a total exposure time between 270 minutes and 399 minutes, respectively. The bacteria were then grown for a 24 hour period and data was acquired. This was performed for E. Coli K12 and S. Epidermidis strains.

ATP Measurement

ATP measurements were conducted in instances where no colonies were visible on the agar plates or bacteria colonies were TNTC. The UltraSnap™ swabs were equilibrated at room temperature (storage for UltraSnap™ swabs are at 21° C.). The surface of the petri dish was swabbed thoroughly, specifically the centre of the plate where bacteria had been pipetted directly. The swab was replaced back into the tube and the liquid-stable reagent from the UltraSnap™ swab was added. The purpose of the addition of the liquid-stable reagent is to facilitate the bioluminescence reaction and optimises sample recovery. The unique liquid-stable reagent gives superior sensitivity and reliable results, with a sensitivity stated of 0.001 fmol. The tube was placed into the Hygiena luminometer within 30 seconds and ATP levels were recorded using a new solid-state photodiode. Photodiodes have the ability to detect and quantify low levels of light. The light emitted is in direct proportion to the amount of ATP present in the sample. Readings less than 10 relative luminescence units (RLU) are considered clean. Readings between 11-29 RLU indicate a warning and readings above 30 RLU indicate a dirty surface. Food manufacturing and healthcare settings both use ATP to determine whether surfaces are clean or not.

Modelling for Cross Contamination Risks

Dose-response model have been derived in order to assess the cross-contamination risk. This modelling helps in the understanding of exposure to pathogens and is crucial in risk assessments (Haas, C. N. (2015) Microbial Dose Response Modeling: Past, Present and Future. Environment Science and Technology 49 1245-1259). An exponential distribution has been developed (Watanabe, T. et al. (2010) Development of a Dose-Response Model for SARS Coronavirus. Risk Analysis 30 7) and is classified as a Generation 1 model i.e. a model that describes the probability of response to exposed dose (Haas 2015).

$$p(d)=1-e^{(-d/k)}$$

Where p(d) is the risk of illness at the dose of d and k is a parameter specific for the pathogen (Watanabe et al. 2010). Parameter k is the probability that a single pathogen will initiate the response (Watanabe et al. 2010). Parameter k is developed for each microorganism (Watanabe et al. 2010). This exponential model will be applied in order to assess the cross-contamination risks.

Results and Discussion

The survival of the E. Coli K12, S. Epidermidis and B. Subtilis was monitored over different time periods using both Protocol I and Protocol II.

Protocol I

The bacterial growth present were TNTC for E. Coli. S. Epidermidis and B. Subtilis on the dark and natural light plates, hence it was not possible to determine the number of colony forming units (CFU). Moreover, no bacteria were visible with the naked eye for the UV light condition for all strains tested. Therefore, in order to assess the surface and any remaining bacteria present and if the surfaces were contaminated, ATP measurements were performed.

| Strain | Setting for UVA | Setting for UVC | Time (hours) | ATP (RLU) Dark | ATP (RLU) UV Light | ATP (RLU) Natural Light |
|---|---|---|---|---|---|---|
| B. Subtilis | 65 mW | 65 mW | 12 | 2431 | 0 | 3893 |
|  | 117 mW | 117 mW | 12 | 7580 | 4 | 7937 |
|  | 42 mW | 65 mW | 12 | 95 | 5 | 1062 |
| E. Coli K12 | 117 mW | 117 mW | 12 | 7004 | 0 | 6031 |
|  | 65 mW | 65 mW | 12 | 5389 | 0 | 7496 |
| S. Epidermis | 117 mW | 117 mW | 12 | 7701 | 0 | 8811 |
|  | 65 mW | 65 mW | 12 | 8272 | 0 | 8899 |
|  | 42 mW | 65 mW | 12 | 8297 | 0 | 3561 |

Table 4: Measurements of ATP in RLU in Dark, Natural Light and UV Light Conditions Using Different Power Levels for UVA and UVC, F, 42 mW and 65 mW, for Different Strains, E. Coli K12. S. Epidermidis and B. Subtilis.

These results show that the combination of UVA and UVC light at power level 42 mW, 117 mW and 65 mW are equally as effective at killing bacteria in the combinations described above (Table 4). The differences in levels of dark and natural light bacteria are due to within day variations, as there will be a small difference in temperature and amount of natural light exposed. Conclusively, it can be demonstrated that a 12 hour period of using any of the aforementioned UVC and UVA power levels shows a nearly 100% reduction in ATP and are below the clean limit of 10 RLU. Herein, we demonstrate this using three different strains of bacteria including E. Coli K12, S. Epidermidis and B. Subtilis.

Protocol II

Distance Measurements

Figure 5:
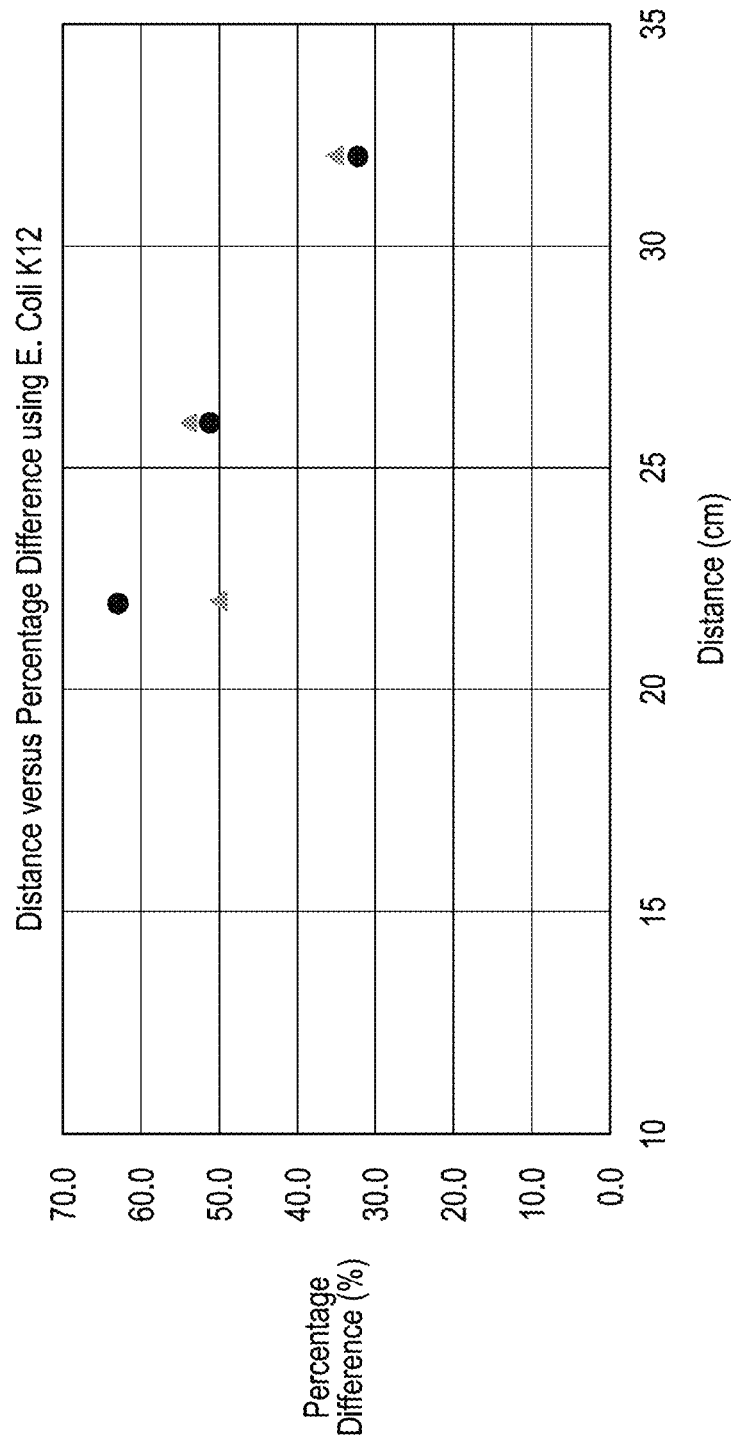
FIG. 5 is the distance of the lamp from the bacteria versus percentage difference (%) in bacteria loading.

Referring now to FIG. 5, the distance of the lamp from the bacteria versus percentage difference (%) in bacteria loading comparing the UV light with the natural light conditions (blue) and dark conditions (grey) using E. Coli K12 as a typical model.

Following 13 iterations of the protocol described above, we observed a 32±3% (average±standard error of the mean (SEM)) reduction in CFU on comparison of the UV exposed bacteria in comparison to the bacteria stored in natural light at 32 cm (FIG. 5). 13 iterations included a total time of 39 minutes of UVC and 360 minutes of UVA exposure. These values may change considering different intensities. Following 13 iterations of the protocol described above, we observed a 35±8% (average±SEM) reduction in CFU on comparison of the UV exposed bacteria in comparison to the bacteria stored in the dark at 32 cm (FIG. 5). These findings are using *E. Coli* K12 as a typical model organism utilising n=36 readings. Similar findings were observed considering *S. Epidermidis* which, using the same aforementioned power levels revealed a 36±2% (average±SEM) reduction in CFU on comparison to UV exposed bacteria compared to bacteria stored in the dark at 32 cm. Similar findings were observed on comparison of CFU of *S. Epidermidis* in light and UV conditions where a 34±5% (average±SEM) reduction was observed in bacteria exposed to UV light. This was concluded using a total of n=86 readings. This shows that the organisms are behaving in the same manner towards the different lighting conditions, which is consistent with previous findings demonstrated in Protocol I.

Moreover, the impact of distance was explored using *E. Coli* K12 as a typical model organism and it was determined that the distance between the lamp and petri dish impacted the percentage growth (see above). This graph concludes the findings of n=207 readings. The closer the lamp to the petri dish, the more intense the reduction observed (FIG. 5). The average SEM levels for these measurements was 4% which shows that there may be some overlap between readings when considering closer distances e.g. from 26 cm to 22 cm. Overall graph 1 reveals a negative linear trend demonstrating the closer the lamp to the petri dish the more reduction observed. The regression value of the light conditions (blue) show a trend of $R^2=0.9993$. The closer the value is to 1 the stronger the relationship between these points. This demonstrates that the distance from the lamp is dependent on bacterial growth.

Iteration Measurements

Moreover, using 10 iterations of the protocol described above we, observed a 6% reduction in bacterial load, on comparison of the bacteria exposed to UV light compared to the dark. This was using *E. Coli* K12 as a typical model with n=10 readings. This shows that differences are observed with less exposure time to the UV light using this pulse sequence and power levels.

Response Modelling for Cross Contamination Risks

With the acquisition of the aforementioned data, models can be fit in order to assess cross contamination risks. We used the exponential model described above in order to assess the impact of the pulsed UV at 32 cm using 39 iterations. Using *E. Coli* K12 which provides a value of $k=9.7\times10^{-9}$ (Du Pont, L. H. et al. (1971) Pathogenesis of *Escherichia coli* Diarrhea. *The New England Journal of Medicine* 285 1-9) we observed that the pulsing programme with the UVA and UVC results in a 50% decrease in cross contamination risk for *E. Coli* K12.

The above technology shows potential applicability to RNA which is specifically important for viruses. The effectiveness of UV has been demonstrated in other virus models such as influenza (Nishisaka-Nonaka, R. et al. (2018) Irradiation by ultraviolet light-emitting diodes inactivates influenza a viruses by inhibiting replication and transcription of viral RNA in host cells *Journal of Photochemistry and Photobiology B: Biology* 189 193-200). It has recently been demonstrated that coronaviruses, specifically MERS-COV, are also impacted by UV-light and are inactivated following exposure to UV light (Keil, S. D. Bowen, R. and Marschner, S. (2016) Inactivation of Middle East respiratory syndrome coronavirus (MERS-COV) in plasma products using a riboflavin-based and ultraviolet light-based photochemical treatment. *Transfusion* 56 2948-2952).

Herein, it has been demonstrated that a pulsed UVA and UVC sequence has the capability to reduce bacterial loadings, using specifically *E. Coli* K12, *S. Epidermidis* and *B. Subtilis*. A reduction in ATP was observed considering 12-hour exposure times using UVA and UVC to all strains using different combinations of power levels, more specifically 65 mW (UVC), 42 mW (UVA) and 117 mW (UVC). Moreover, pulse experiments using UVA at 42 mW and UVC at 65 mW revealed a reduction in *E. Coli* K12 and *S. Epidermidis* at a 32 cm distance comparatively to natural light and dark settings. Moreover, distance of the UV lamp was revealed to impact the bacterial growth and an $R^2=0.9993$ was obtained demonstrating this relationship. Modelling revealed a 50% reduction in cross contamination risk.

As many changes can be made to the preferred embodiment of the disclosure without departing from the scope thereof: it is intended that all matter contained herein be considered illustrative and not in a limiting sense.

The invention claimed is:

1. A UVA/UVC system for reducing levels, on an inanimate surface, and
    inhibiting further growth of at least one pathogen on said inanimate surface, wherein said system has no deleterious effects on a human eye, wherein said system comprises:
    i) an inanimate surface;
    ii) at least one UVA light source at least 22 centimeters from said inanimate surface;
    iii) at least one UVC light source at least 22 centimeters from said inanimate surface; and
    iv) at least one controller connected to each of said at least one UVA light source and said at least one UVC light source, for controlling at least one parameter of each of said UVA light source and UVC light source selected from light source, light intensity, radiated power level, wavelength, exposure time and combinations thereof; wherein said at least one UVC light source emits UVC light to a surface for a period of time reducing the level of said at least one pathogen on said inanimate surface to a level that is safe to humans, and said at least one UVA light source emits UVA light to said inanimate surface for a period of time inhibiting growth of said at least one pathogen on said inanimate surface, such that during the time said at least one UVC light source and said at least one UVA light source is emitting on said inanimate surface, radiation levels from said at least one UVC light source and said at least one UVA light source is safe to human eyes in public areas; wherein when said at least one UVC light source is emitting UVC light to said inanimate surface, said at least one UVA light is off, and when said at least one UVA light source is emitting light to said inanimate surface, said at least one UVC light source is off; wherein cycling between said at least one UVC light source and said at least one UVA light source is controlled by said at least one controller; wherein said at least one UVA light source has an operating wavelength of from about 385 nanometers (nm) to about 400 nm and a power rating of from about 10 milliwatts (mW) to about 100 watts (W); and said at least one UVC light source has an operating wavelength of from about 275 nm to about 295 nm and a power rating from about 10 mW to about 100 W wherein said UVA power rating remains constant during the exposure time inhibiting growth of said at least one pathogen on said inanimate surface and said UVC power rating remains constant during the exposure time reducing the level of said at least one pathogen on said inanimate surface, and said exposure time of emitting each of said i) UVA light source; and ii) said UVC light source is regulated on and/or off based solely on time.

2. The system of claim 1, wherein said at least one UVC light source has an operating wavelength of about 275 nanometers (nm).

3. The system of claim 1 wherein said at least one UVA light source has an operating wavelength of about 400 nm.

4. The system of claim 1 wherein said at least one UVC light source is a light emitting diode (LED).

5. The system of claim 1 wherein said at least one UVA light source is a LED.

6. The system of claim 1 wherein the at least one controller automatically cycles between emitting light from said at least one UVA light source and from said at least one UVC light source.

7. The system of claim 1 wherein said at least one UVC light source has an emission at a power level and time duration to reduce at least one pathogen on said inanimate surface exposed to said at least one UVC light source.

8. The system of claim 1 wherein the power level is selected to ensure the radiated emission from said at least one UVC light source is at a safe level for human eyes.

9. The system of claim 1 wherein the time duration is selected to ensure the radiated emission from said at least one UVC light source is at a safe exposure time for human eyes.

10. The system of claim 1 wherein said at least one UVA light source has an emission at a power level to inhibit growth of at least one pathogen on said inanimate surface exposed to said at least one UVC light source.

11. The system of claim 1, wherein said at least one UVC light source has a power rating of 244 mW.

12. The system of claim 1, wherein said at least one UVA light source has a power rating of 20 mW.

13. The system of claim 1 wherein said system reduces the level of at least one pathogen on said inanimate surface exposed to said system by 1 to 100%.

14. The system of claim 1 wherein said system reduces the level of at least one pathogen on said inanimate surface exposed to said system by 10 to 20%.

15. The system of claim 1, for the reduction of at least one pathogen selected from the group consisting of *E. Coli* K12, *S. Epidermidis* and *B. Subtilis*.

16. The system of claim 1 wherein said inanimate surface is selected from the group consisting of countertops, hard counters, wood counters, concrete, plastic, rubber, leather, and combinations thereof.

17. The system of claim 1 wherein said at least one UVA light source has a constant power level of 15.6 $Jm^{-2}$ and said at least one UVC light source has a constant power level of 28.6 $Jm^{-2}$ at 1 meter from the at least one UVA light source and the at least one UVC light source, respectively, and said exposure time of emitting each of said i) UVA light source; and ii) said UVC light source is regulated on and/or off based solely on time.

18. The system of claim 1 wherein said at least one UVA light source has a power level of 53 $Jm^{-2}$ and said at least one UVC light source has a power level of 235 $Jm^{-2}$ at 20 centimeters from the at least one UVA light source and the at least one UVC light source, respectively, and said exposure time of emitting each of said i) UVA light source; and ii) said UVC light source is regulated on and/or off based solely on time.

19. The system of claim 1 wherein said system has no deleterious effects on human epidermis and dermis.

* * * * *